US010247723B2

United States Patent
Roberts

(10) Patent No.: US 10,247,723 B2
(45) Date of Patent: Apr. 2, 2019

(54) LIGHTING SYSTEMS AND METHODS OF USING LIGHTING SYSTEMS FOR IN VIRTO POTENCY ASSAY FOR PHOTOFRIN

(71) Applicant: Concordia Laboratories Inc., St. Michael (BB)

(72) Inventor: Michael Scot Roberts, Myersville, MD (US)

(73) Assignee: Concordia Laboratories Inc., St. Michael (BB)

( * ) Notice: Subject to any disclaimer, the term of this patent is extended or adjusted under 35 U.S.C. 154(b) by 105 days.

(21) Appl. No.: 15/175,013

(22) Filed: Jun. 6, 2016

(65) Prior Publication Data

US 2016/0282332 A1 Sep. 29, 2016

Related U.S. Application Data

(63) Continuation of application No. 13/689,490, filed on Nov. 29, 2012, now Pat. No. 9,371,555.
(Continued)

(51) Int. Cl.
*C12N 13/00* (2006.01)
*F21V 13/02* (2006.01)
(Continued)

(52) U.S. Cl.
CPC ......... *G01N 33/5011* (2013.01); *A61K 41/00* (2013.01); *C12N 13/00* (2013.01);
(Continued)

(58) Field of Classification Search
CPC ......... G01N 21/255; G01N 2201/061; G01N 2201/0633; G01N 2201/0686;
(Continued)

(56) References Cited

U.S. PATENT DOCUMENTS 4,890,208 A * 12/1989 Izenour ............... F21V 9/04
362/294
5,205,291 A 4/1993 Potter
(Continued)

FOREIGN PATENT DOCUMENTS

WO 1988/01730 A1 3/1988
WO 1997/020596 A1 6/1997
(Continued)

OTHER PUBLICATIONS

Lipson, Richard L., et al., "Hematoporphyrin Derivative for Detection and Management of Cancer," Cancer, 1967, vol. 20, p. 2235.
(Continued)

*Primary Examiner* — Anh T Mai
*Assistant Examiner* — Arman B Fallahkhair
(74) *Attorney, Agent, or Firm* — McDonnell Boehnen Hulbert & Berghoff LLP

(57) ABSTRACT

Presently disclosed is a lighting system and methods of using the lighting system for in vitro potency assay for photofrin. The lighting system includes a lamp housing, a first lens, an infrared absorbing filter, an optical filter, and a second lens. The lamp housing includes a lamp and a light-port. In operation, broad spectrum light from the lamp exits the lamp housing by passing through the light-port. The first lens then collimates the broad spectrum light that exits the lamp housing through the light-port. The infrared absorbing filter then passes a first portion of the collimated broad spectrum light to the optical filter and absorbs infrared light of the broad spectrum light. The optical filter then passes a second portion of the collimated broad spectrum light to the second lens. The second lens then disperses the second portion of the collimated light to provide uniform irradiation of a cell culture plate. A method of using the
(Continued)

lighting system for studying a photosensitizer is also disclosed.

19 Claims, 11 Drawing Sheets

Related U.S. Application Data

(60) Provisional application No. 61/654,375, filed on Jun. 1, 2012.

(51) Int. Cl.

| | |
|---|---|
| G01N 33/50 | (2006.01) |
| C12Q 1/22 | (2006.01) |
| G01N 21/25 | (2006.01) |
| A61K 41/00 | (2006.01) |
| F21V 5/00 | (2018.01) |
| F21V 5/04 | (2006.01) |
| F21V 7/00 | (2006.01) |
| F21V 9/04 | (2018.01) |
| F21V 13/14 | (2006.01) |

(52) U.S. Cl.
CPC .............. *C12Q 1/22* (2013.01); *F21V 5/00* (2013.01); *F21V 5/04* (2013.01); *F21V 7/00* (2013.01); *F21V 9/04* (2013.01); *F21V 13/02* (2013.01); *F21V 13/14* (2013.01); *G01N 21/255* (2013.01); *G01N 2201/061* (2013.01); *G01N 2201/0633* (2013.01); *G01N 2201/0686* (2013.01)

(58) Field of Classification Search
CPC ......... G01N 33/5011; F21V 5/00; F21V 5/04; F21V 7/00; F21V 9/04; F21V 13/02; F21V 13/14; C12N 13/00; A61K 41/00; C12Q 1/22

See application file for complete search history.

(56) References Cited

U.S. PATENT DOCUMENTS

| | | | |
|---|---|---|---|
| 5,244,914 A | 7/1993 | Clauss et al. | |
| 5,238,940 A | 8/1993 | Liu et al. | |
| 5,341,676 A | 8/1994 | Gouterman et al. | |
| 5,377,003 A * | 12/1994 | Lewis ................ | G01J 3/2823 250/339.02 |
| 5,407,808 A | 4/1995 | Hailing et al. | |
| 5,438,071 A | 8/1995 | Clauss et al. | |
| 5,782,895 A * | 7/1998 | Zarate ................ | A61N 5/062 250/504 R |
| 5,844,638 A | 12/1998 | Ooi et al. | |
| 6,036,941 A | 3/2000 | Bottiroli et al. | |
| 6,429,936 B1 * | 8/2002 | Scaduto ............ | G01N 21/6458 250/458.1 |
| 6,478,732 B2 | 11/2002 | Adachi | |
| 6,596,257 B2 | 7/2003 | Bryan | |
| 6,984,656 B2 | 1/2006 | Detty et al. | |
| 7,371,742 B2 | 5/2008 | Grierson et al. | |
| 7,580,185 B2 * | 8/2009 | Haisch ................ | A61B 5/0066 250/461.2 |
| 7,700,717 B2 | 4/2010 | Bonasera et al. | |
| 8,040,599 B2 * | 10/2011 | Steffen ................ | G02B 21/16 359/368 |
| 8,139,210 B2 * | 3/2012 | Baek ................ | G01N 21/6452 356/22 |
| 8,147,190 B2 | 4/2012 | Tsypkaykin et al. | |
| 8,248,614 B2 * | 8/2012 | Mann ................ | G01B 9/021 356/485 |
| 8,659,651 B2 * | 2/2014 | Jess ................ | G02B 21/0012 348/79 |
| 9,371,555 B2 * | 6/2016 | Roberts ................ | C12Q 1/22 |

| | | |
|---|---|---|
| 2003/0004556 A1 | 1/2003 | McDaniel |
| 2003/0032204 A1 | 2/2003 | Walt et al. |
| 2004/0109231 A1 | 6/2004 | Haisch et al. |
| 2005/0209193 A1 | 9/2005 | Keller |
| 2006/0013454 A1 | 1/2006 | Flewelling et al. |
| 2006/0145098 A1 | 7/2006 | Baek et al. |
| 2007/0299046 A1 | 12/2007 | Brooks et al. |
| 2008/0014248 A1 | 1/2008 | Park et al. |
| 2008/0114419 A1 | 5/2008 | Crowley |
| 2008/0234363 A1 | 9/2008 | Benitez et al. |
| 2009/0081209 A1 | 3/2009 | Emtage et al. |
| 2009/0306101 A1 | 12/2009 | Solca et al. |
| 2010/0087534 A1 | 4/2010 | Ortner et al. |
| 2010/0120668 A1 | 5/2010 | Wolgen |
| 2010/0145416 A1 | 6/2010 | Kang |
| 2010/0174223 A1 | 7/2010 | Sakamoto et al. |
| 2010/0184818 A1 | 7/2010 | Wharton et al. |
| 2010/0312312 A1 | 12/2010 | Jones |
| 2011/0064752 A1 | 3/2011 | Hutchinson et al. |
| 2011/0250143 A1 | 10/2011 | Da Silva Arnaut Moreira et al. |

FOREIGN PATENT DOCUMENTS

| | | |
|---|---|---|
| WO | 2007/004045 A2 | 1/2007 |
| WO | 2011/031955 A2 | 3/2011 |
| WO | 2011/161065 A1 | 12/2011 |

OTHER PUBLICATIONS

Dougherty, T.J., et al., "Photoradiation Therapy. II. Cure of Animal Tumors with Hematoporphyrin and Light," Journal of the National Cancer Institute, Jul. 1975, vol. 55(1), p. 115.

Dougherty, T.J., "Hematoporphyrin as a Photosensitizer of Tumors," Photochemistry and Photobiology, 1983, vol. 38(3), pp. 377-379.

Ho, Yau-Kwan, et. al., "Activity and Physicochemical Properties of Photofrin(R)," Photochemistry and Photobiology, 1991, vol. 54(1), pp. 83-87.

Pandey, Ravindra K., et al., "Porphyrin Dimers as Photosensitizers in Photodynamic Therapy," J. Med. Chem., 1990, vol. 33, p. 2032.

Ortner, M.A., "Photodynamic Therapy for Cholangiocarcinoma," Lasers Surg. Med., Sep. 2011, vol. 43(7), pp. 776-780. (Abstract only).

Talreja, J.P., et al., "Photodynamic Therapy for Unresectable Cholangiocarcinoma: Contribution of Single Operator Cholangioscopy for Targeted Treatment," Photochem Photobiol Sci., Jul. 2011, vol. 10(7), pp. 1233-1238. (Abstract only).

Choi, H.J., et al., "Clinical Feasibility of Direct Peroral Cholangioscopy-guided Photodynamic Therapy for Inoperable Cholangiocarcinoma Performed by Using an Ultra-slim Upper Endoscope (with videos)," Gastrointest Endosc., Apr. 2011, vol. 73(4), pp. 808-813. (Abstract only).

Ortner, M.A., et al., "The Pharmacokinetics and Safety of Porfimer after Repeated Administration 30-45 Days Apart to Patients Undergoing Photodynamic Therapy," Ailment Pharmacol Ther., Sep. 2010, vol. 32(6) pp. 821-827. (Abstract only).

Talreja, J.P., et al., "Photodynamic Therapy for Cholangiocarcinoma," Gut and Liver, Sep. 2010, vol. 4(Suppl 1), pp. S62-S66. (Abstract only).

Quyn A.J., et al., "Photodynamic Therapy is Associated with an Improvement in Survival in Patients with Irresectable Hilar Cholangiocarcinoma.", HPB (Oxford), Nov. 2009, vol. 11(7), pp. 570-577. (Abstract only).

Cao, L.Q., et al., "Hematoporphyrin Derivative-Mediated Photodynamic Therapy Inhibits Tumor Growth in Human Cholangiocarcinoma In Vitro and In Vivo.", Hepatol Res., Dec. 2009, vol. 39(12), pp. 1190-1197. (Abstract only).

Ortner, M.A., "Photodynamic Therapy for cholangiocarcinoma: Overview and New Developments," Curr Opin Gastroentereol., Sep. 2009, vol. 25(5), pp. 472-476. (Abstract only).

Kiesslich, T., et al., "Photodynamic Therapy for Non-resectable Perihilar Cholangiocarcinoma," Photochem Photobiol Sci., Jan. 2009, vol. 8(1), pp. 23-30. (Abstract only).

Zoepf, T., "Photodynamic Therapy of Cholangiocarcinoma," HPB (Oxford), 2008, vol. 10(3), pp. 161-163. (Abstract only).

(56) References Cited

OTHER PUBLICATIONS

Kahaleh, M., et al., "Unresectable Cholangiocarcinoma: Comparison of Survival in Biliary Stenting Alone Versus Stenting with Photodynamic," Clin Gastroenterol Hepatol, Mar. 2008, vol. 6(3), pp. 290-297. (Abstract only).

Harewood, G.C., et al., "Pilot Study to Assess Patient Outcomes Following Endoscopic Application of Photodynamic Therapy for Advanced Cholangiocarcinoma," J Gastroenterol Hepatol, Mar. 2005, vol. 20(3), pp. 415-20. (Abstract only).

Ortner, M.E., et al., "Successful Photodynamic Therapy for Nonresectable Cholangiocarcinoma: A Randomized Prospective Study," Gastroenterology, Nov. 2003, vol. 125(5), pp. 1355-1363. (Abstract only).

Ortner, M., "Photodynamic Therapy for Cholangiocarcinoma," J Hepatobiliary Pancreat Surg., 2001, vol. 8(2), pp. 137-139. (Abstract only).

Ortner, M., "Photodynamic Therapy in the Biliary Tract," Curr Gastroenterol Rep., Apr. 2001, vol. 3(2), pp. 154-159. (Abstract only).

Ortner, M.A., "Photodynamic Therapy of Cholangiocarcinoma Cancer," Gastrointest Endosc Clin N Am., Jul. 2000, vol. 10(3), pp. 481-486. (Abstract only).

Ortner, M.A., et al., "Photodynamic Therapy of Nonresectable Cholangiocarcinoma," Gastroenterology, Mar. 1998, vol. 114(3), pp. 536-542. (Abstract only).

Pahernik, S.A., et al., "Distribution and Pharmacokinetics of Photofrin in Human Bile Duct Cancer," J Photochem Photobiol B., Nov. 1998, vol. 47(1), pp. 58-62.

Matthews W., et al., "In Vitro Photodynamic Therapy of Human Lung Cancer: Investigation of Dose-rate Effects," Cancer Res., Apr. 1, 1989, vol. 49(7), pp. 1718-1721.

Matthews W., et al., "In Vitro Photodynamic Therapy of Human Lung Cancer," J Surg Res., Sep. 1989, vol. 47(3), pp. 276-281. (Abstract only).

Saczko, J., et al., "Photooxidative Action in Cancer and Normal Cells Induced by the Use of Photofrin in Photodynamic Therapy," Folia Biol (Praha), 2008, vol. 54(1), pp. 24-29.

De Beule, P.A.A., et al., "Development of Multi-Dimensional Fluorescence Instrumentation for Biomedical Applications," Imperial College London (University of London), Sep. 2007, pp. 1-114.

Lange, N., et al., "A New Drug-Screening Procedure for Photosensitizing Agents Used in Photodynamic Therapy for CNV," IOVS, Jan. 2011, vol. 42(1), pp. 38-46.

Serra, A.C., et al., "Halogen Atom Effect on Photophysical and Photodynamic Characteristics of Derivatives of 5,10,15,20-tetrakis(3-hydroxyphenyl)porphyrin", Journal of Photochemistry and Photobiology B: Biology, vol. 92(1), Jul. 24, 2008, pp. 59-65.

Pandey, R.K., et al., "Syntheses and Photosensitizing Activity of Porphyrins Joined with Ester Linkages", Cancer Research, Apr. 15, 1989, vol. 49, pp. 2042-2047.

International Preliminary Report on Patentability, International Bureau, dated Dec. 11, 2014, pp. 1-7.

\* cited by examiner

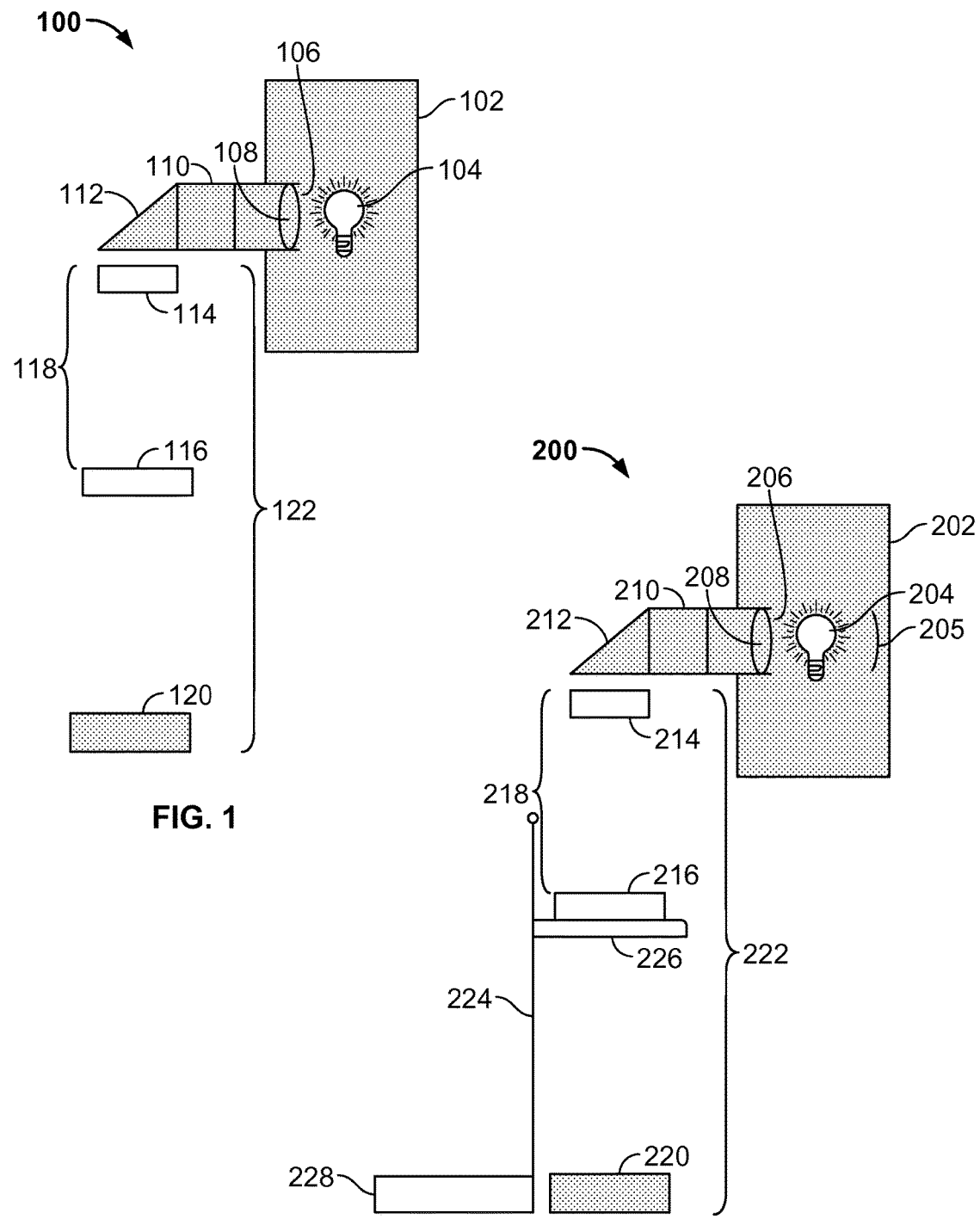

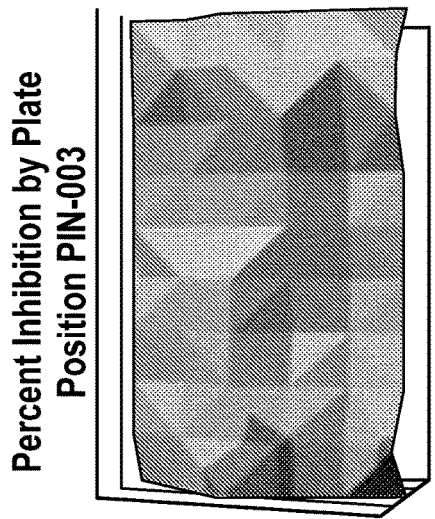
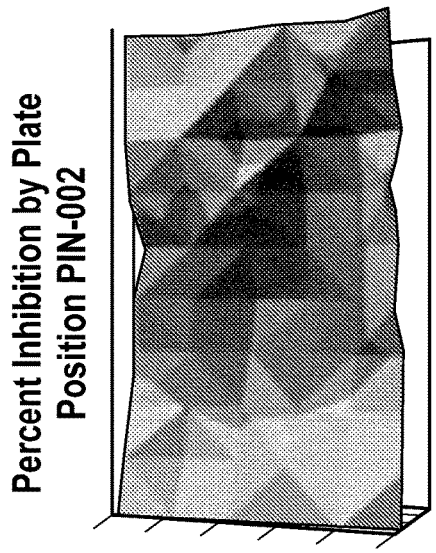
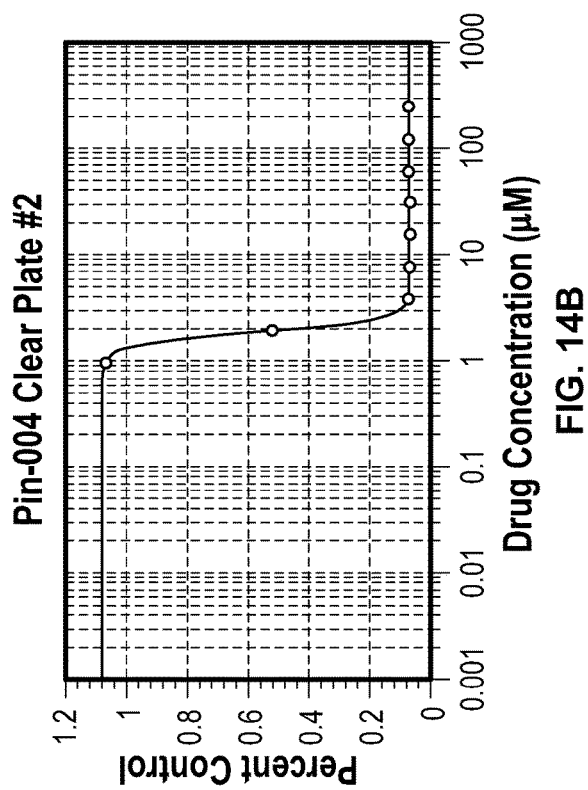
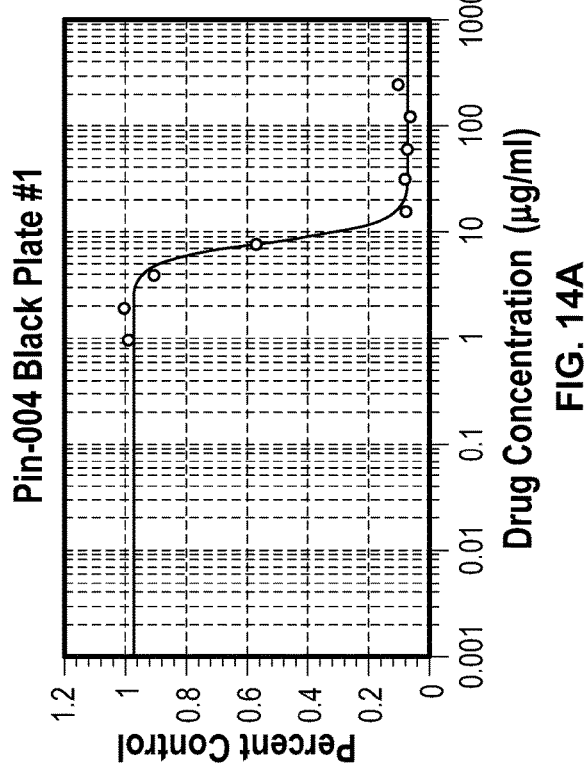
FIG. 13
FIG. 14A
FIG. 14B

LIGHTING SYSTEMS AND METHODS OF USING LIGHTING SYSTEMS FOR IN VIRTO POTENCY ASSAY FOR PHOTOFRIN

CROSS-REFERENCE TO RELATED APPLICATION

This application is a continuation of allowed U.S. patent application Ser. No. 13/689,490, filed Nov. 29, 2012, now U.S. Pat. No. 9,371,555, which claims the benefit of U.S. Provisional Application No. 61/654,375 filed Jun. 1, 2012, which are incorporated by reference in their entirety.

BACKGROUND

Unless otherwise indicated herein, the materials in this section are not prior art to the claims and are not admitted to be prior art by inclusion in this section.

Photodynamic therapy can be used for the treatment of neoplastic and non-neoplastic diseases. This therapy involves the administration of a photosensitizer, such as a porphyrin, and subsequent irradiation of the cells treated with the photosensitizer at a proper dose and wavelength.

Photofrin® is an FDA-approved porphyrin-based antineoplastic agent that accumulates in tumor tissue following systematic administration where it can then be site-specifically irradiated with light at 630 nanometers causing the formation of reactive oxygen species and the death of the surrounding tumor mass. Before being released for clinical use, manufactured lots of Photofrin® must be shown to possess the expected degree of activity, i.e., the potency of the lot must be verified. Lot release assays for biologic drug activity, including potency assays, can either be in vivo or in vitro assays and should measure the activity of the drug thought to be responsible for the clinical effect.

SUMMARY

In one respect, the present invention provides a lighting system comprising: a lamp housing including a lamp and a light-port, wherein broad spectrum light from the lamp exits the lamp housing through the light-port; a first lens to collimate the broad spectrum light that exits the lamp housing through the light-port; an infrared absorbing filter to pass a first portion of the collimated broad spectrum light and absorb infrared light of the broad spectrum light that passes through the light-port and that is collimated by the first lens, wherein the first portion of the collimated broad spectrum light comprises a second portion of the collimated broad spectrum light; an optical filter to pass the second portion of the collimated broad spectrum light after the first portion of the collimated broad spectrum light reaches the optical filter; and a second lens to disperse the second portion of the collimated light that passed through the optical filter.

In another respect, the present invention provides a lighting system, wherein the first lens comprises a condenser lens.

In another respect, the present invention provides a lighting system, wherein the first lens comprises a Fresnel lens.

In another respect, the present invention provides a lighting system, wherein the lamp comprises a xenon arc lamp.

In another respect, the present invention provides the lighting system, wherein the optical filter comprises an infrared blocking filter and a short pass filter.

In another respect, the present invention provides a lighting system, wherein the infrared blocking filter absorbs residual infrared light of the first portion of the collimated broad spectrum light, and wherein the short pass filter filters out light of the first portion of the collimated broad spectrum light of wavelengths greater than 650 nm.

In another respect, the present invention provides a lighting system comprising: a reflector to reflect the first portion of the collimated broad spectrum light that passes through the infrared absorbing filter.

In another respect, the present invention provides a lighting system, wherein the first portion of the collimated broad spectrum light reflected by the reflector propagates to the infrared blocking filter, and wherein the second portion of the collimated broad spectrum light that propagates to the infrared blocking filter, as part of the first portion of the collimated broad spectrum light, passes through the infrared blocking filter and then through the short pass filter.

In another respect, the present invention provides a lighting system, wherein the first portion of the collimated broad spectrum light reflected by the reflector propagates to the short pass filter, and wherein the second portion of the collimated broad spectrum light that propagates to the short pass filter, as part of the first portion of the collimated broad spectrum light, passes through the short pass filter and then through the infrared blocking filter.

In another respect, the present invention provides a lighting system, wherein the reflector comprises a dichroic mirror.

In another respect, the present invention provides a lighting system, wherein the dichroic mirror absorbs at least a portion of infrared light that passes through the light-port and the infrared absorbing filter.

In another respect, the present invention provides a lighting system, wherein the optical filter comprises a band-pass filter.

In another respect, the present invention provides a lighting system, wherein the lamp housing is sealed so that the broad spectrum light from the lamp exits the lamp housing only through the light-port.

In another respect, the present invention provides a lighting system, wherein the lamp housing is sealed so that less than 1% of the broad spectrum light from the lamp exits the lamp housing other than through the light-port.

In another respect, the present invention provides a lighting system comprising: a ring stand; a first support ring removably attached to the ring stand; and a base.

In another respect, the present invention provides a lighting system, wherein the second lens comprises a first dispersing lens and a second dispersing lens; and wherein the first support ring holds the first dispersing lens and the second dispersing lens in place.

In another respect, the present invention provides a lighting system, wherein the first dispersing lens comprises a first plano convex lens; wherein the second dispersing lens comprises a second plano convex lens; wherein the first plano convex lens comprises a first plano side and a first convex side; wherein the second plano convex lens comprises a second plano side and a second convex side; and wherein the first convex side is adjacent to the second convex side with a gap between the first convex side and the second convex side.

In another respect, the present invention provides a lighting system, wherein the gap is within the range of 2 millimeters and 4 millimeters, inclusive.

In another respect, the present invention provides a lighting system, wherein the gap is 3 millimeters.

In another respect, the present invention provides a lighting system, wherein the infrared absorbing filter comprises an infrared absorbing liquid filter.

In another respect, the present invention provides a lighting system, wherein the infrared absorbing liquid filter absorbs between 90% and 100%, inclusive, of the infrared light of the broad spectrum light that that passes through the light-port.

In another respect, the present invention provides a lighting system comprising: a wall, wherein the light-port is located within the wall, and wherein a position of the second lens is adjustable in at least one of a direction parallel to the wall and a direction perpendicular to the wall.

In another respect, the present invention provides a lighting system comprising: a shelf, and a lens slider including a first hole for passing light; wherein the shelf comprises a shelf riser parallel to the wall, wherein the shelf comprises a shelf top perpendicular to the wall, wherein the shelf top includes a second hole for passing light, wherein the second lens is removably attached to the lens slider, wherein the lens slider is removably attached to the shelf top, and wherein at least a portion of the first hole is above or below at least a portion of the second hole.

In another respect, the present invention provides a lighting system, wherein the shelf riser comprises a first parallel adjustment slot; and wherein the shelf top comprises a first perpendicular adjustment slot.

In another respect, the present invention provides a lighting system, wherein the wall comprises a base wall and a wall of the lamp housing.

In another respect, the present invention provides a lighting system, wherein the lamp housing comprises a top, wherein the light-port is within the top, wherein the first lens is within the light-port, and wherein the infrared absorbing filter, the optical filter, and the second lens are located at positions above the top.

In another respect, the present invention provides a lighting system, wherein the lamp housing comprises a bottom, wherein the light-port is within the bottom, wherein the first lens is within the light-port, and wherein the infrared absorbing filter, the optical filter, and the second lens are located at positions below the bottom.

In one aspect, the present invention provides a method comprising using a lighting system to irradiate contents of a cell culture plate.

In another aspect, the present invention provides a method of using a lighting system to irradiate contents of a cell culture plate, wherein the cell culture plate comprises a photosensitizer.

In another aspect, the present invention provides a method for studying a photosensitizer comprising: adding the photosensitizer to a portion of wells on a cell culture plate to form photosensitizer assay wells, the wells comprising carcinoma cells; incubating the photosensitizer assay wells for a first predetermined time period; optionally washing the photosensitizer assay wells; irradiating the photosensitizer assay wells with a lighting system at a predetermined wavelength to form irradiated wells, wherein each well is uniformly irradiated; incubating the irradiated wells for a second predetermined time period; and determining percent viability of the carcinoma cells contained in the wells.

In yet another aspect, the present invention provides a method for studying a photosensitizer, wherein the step of washing the photosensitizer assay wells is mandatory.

In another aspect, the present invention provides a method for studying a photosensitizer, wherein a remaining portion of the wells are control wells.

In another aspect, the present invention provides a method for studying a photosensitizer, wherein a portion of the wells contain a reference drug used for comparison.

In another aspect, the present invention provides a method for studying a photosensitizer, wherein the photosensitizer is a porphyrin-based anti-neoplastic agent.

In another aspect, the present invention provides a method for studying a photosensitizer, wherein the porphyrin-based anti-neoplastic agent is porfimer sodium.

In yet another aspect, the present invention provides a method for studying a photosensitizer, wherein the photosensitizer assay wells are irradiated with light within a range of 400 nm to 650 nm.

In another aspect, the present invention provides a method for studying a photosensitizer, wherein the carcinoma cells are A549 human lung carcinoma cells.

In another aspect, the present invention provides a method for studying a photosensitizer, wherein the irradiating step is standardized.

In another aspect, the present invention provides a method for studying a photosensitizer, wherein the cell culture plate is an opaque black plate.

These as well as other aspects, advantages, and alternatives will become apparent to those of ordinary skill in the art by reading the following detailed description, with reference where appropriate to the accompanying drawings. Further, it should be understood that this summary and the other description provided throughout this document is provided to explain the invention by way of example and is not intended to be limiting.

BRIEF DESCRIPTION OF THE DRAWINGS

Example embodiments of the invention are described herein with reference to the drawings, wherein like parts are designated by like reference numerals, and wherein:

FIG. 1 is a block diagram of a lighting system;

FIG. 2 is a block diagram of an alternative embodiment lighting system;

FIG. 13 is a graphical representation of homogeneity of irradiance;

FIG. 14A is a graphical representation of dose response of Photofrin® from 250-0.977 µg/mL in a black plate; and FIG. 14B is a graphical representation of dose response of Photofrin® from 250-0.977 µg/mL in a clear plate.

DETAILED DESCRIPTION OF THE INVENTION

1. Example Architecture

Figure 3:
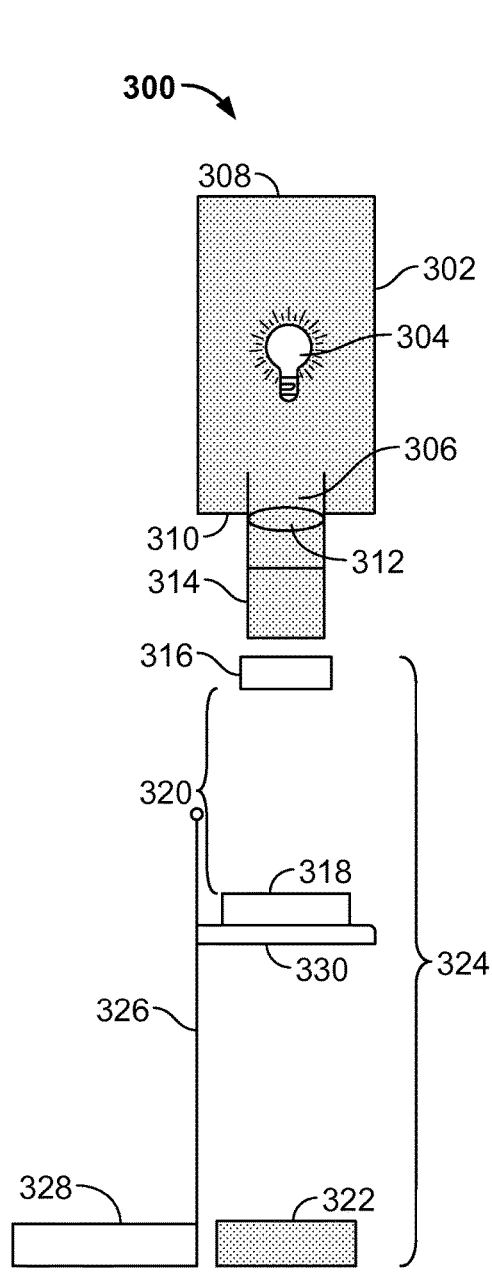
FIG. 3 is a block diagram of another embodiment lighting system.

In this description, the articles "a" or "an" are used to introduce elements of the example embodiments. The intent of using those articles is that there is one or more of the elements. The intent of using the conjunction "or" within a described list of at least two terms is to indicate any of the listed terms or any combination of the listed terms. The use of ordinal numbers such as "first," "second," "third" and so on is to distinguish respective elements rather than to denote a particular order of those elements.

FIG. 1 illustrates an embodiment of a lighting system generally designated 100 and components thereof. The lighting system 100 includes a lamp housing 102, a first lens 108, an infrared absorbing filter 110, a reflector 112, an optical filter 114, a second lens 116, and a cell culture plate 120. The lamp housing 102 includes a lamp 104 and a light-port 106.

In the lighting system 100, the first lens 108 is within the light-port 106. The infrared absorbing filter 110 is connected to the light-port 106. The reflector 112 is connected to the infrared absorbing filter 110. The optical filter 114 is connected to the reflector 112. The second lens 116 is located a distance 118 from the optical filter 114. The cell culture plate 120 is located a distance 122 from the optical filter 114.

In operation, the cell culture plate 120, as well as contents of the cell culture plate 120, is irradiated with light from the lamp 104. The lamp 104 may be one or more 1000 watt xenon arc lamps. First, broad spectrum light from the lamp 104 exits the lamp housing 102 by passing through the light-port 106. The lamp housing 102 may be sealed so that the broad spectrum light from the lamp 104 exits the lamp housing 102 only through the light-port 106. Alternatively, the lamp housing 102 may be sealed so that less than 1% of the broad spectrum light from the lamp 104 exits the lamp housing 102 other than through the light-port 106.

After the broad spectrum light exits the lamp housing 102 by passing through the light-port 106, the broad spectrum light is collimated by the first lens 108. The first lens 108 can be arranged in various configurations. In a first configuration, the first lens 108 may be a 50 millimeter (mm) focal length condenser lens. In that first configuration or in another configuration, the first lens 108 may be a Fresnel lens. Moreover, in that first configuration or in another configuration, the first lens 108 may have a diameter of 2 or 3 inches (in). Other examples of the diameter of the first lens 108 are possible. In a second example configuration, the first lens 108 can comprise two or more lenses. In accordance with one or more of these example embodiments of the first lens 108, the first lens 108 can comprise a lens holder configured for supporting a lens, such as a glass lens, and for connecting the first lens 108 to another component of the lighting system 100, such as infrared absorbing filter 110, the light-port 106, the reflector 112, or a spacer.

After the broad spectrum light is collimated by the first lens 108, the broad spectrum light reaches the infrared absorbing filter 110. The infrared absorbing filter 110 absorbs infrared light of the broad spectrum light. The infrared absorbing filter 110 also passes a first portion of the collimated broad spectrum light to the reflector 112.

After the first portion of the collimated broad spectrum light is passed by the infrared absorbing filter 110 to the reflector 112, the reflector 112 reflects the first portion of the collimated broad spectrum light. The first portion of the collimated broad spectrum light then propagates to the optical filter 114. Alternatively, the reflector 112 may reflect only a portion of the first portion of the collimated broad spectrum light, and the portion of the first portion of the collimated broad spectrum light then propagates to the optical filter 114. The reflector 112 may be one or more dichroic mirrors. The first portion of the collimated broad spectrum light that is reflected by the reflector 112 to the optical filter 114 may have a wavelength in a given range. For example, the collimated broad spectrum light may have a given range of 400 nanometers (nm) to 700 nm. Other given ranges are possible. In some embodiments, the reflector 112 absorbs at least a portion of infrared light or at least a portion of ultraviolet light of the collimated broad spectrum light. With this arrangement, the reflector 112 functions like an optical filter by passing only visible light to the optical filter 114.

After the first portion of the collimated broad spectrum light propagates to the optical filter 114, the optical filter 114 passes a second portion of the collimated broad spectrum light to the second lens 116. The optical filter 114 may be one or more band-pass filters. As an example, the light passed to the second lens 116 may be collimated light within the range of 400 nm to 630 nm (i.e., no infrared or ultraviolet light). Different ranges can be passed to the second lens 116 depending on what light is reflected by the reflector 112 and passed by the optical filter 114. As another example, the range of wavelengths can be any variety of ranges, such as between about 595 nm and about 645 nm, between about 620 nm and about 640 nm, between about 615 nm and about 645 nm, or between about 610 nm and about 650 nm. Narrower band-pass filters can be used to reduce the range. The range of wavelengths can be centered on a given wavelength, such as 630 nm. A different center wavelength can be selected by changing components of the lighting system 100, such as the reflector 112 and the optical filter 114.

After the second portion of the collimated broad spectrum light is passed by the optical filter 114 to the second lens 116, the second lens 116 disperses the second portion of the collimated broad spectrum light to the cell culture plate 120. The second lens 116 can be arranged in various configurations. In a first configuration, the second lens 116 may have a diameter of 3 in. Other examples of the diameter of the second lens 116 are possible. In a second example configuration, the second lens 116 can comprise two or more lenses. In accordance with one or more of these example embodiments of the second lens 116, the second lens 116 can comprise a lens holder configured for supporting a lens, such as a glass lens.

The cell culture plate 120 can be arranged in various configurations. In general, the cell culture plate 120 can have a bottom area, a top area, and a vertical wall extending from the bottom area to the top area. The bottom area, the top area, and the vertical wall can each be transparent or opaque. For purposes of this description, transparent can be clear transparent but is not so limited. For purposes of this description, opaque can be black opaque but is not so limited. The bottom area and vertical wall can be made of the same material such as polystyrene or some other material. The bottom area and vertical wall can have an external surface and an internal surface. Contents placed within the cell culture plate can contact the internal surfaces of the bottom area and the vertical wall.

The top area can be open or opened to allow contents to be placed within cell culture plate 120 and to allow those contents to be subsequently removed. The top area can include a removable cover, such as a transparent cover. The cell culture plate 120 can comprise multiple wells, such as 2, 4, 6, 12, 24, 48, or 96 wells. The multiple wells can be transparent or opaque. The multiple wells can be made of polystyrene or some other material. The cell culture plate 120 can be a petri dish.

The bottom area, the top area, and vertical wall can be arranged to provide the cell culture plate 120 with a defined shape. In one respect, cell culture plate 120 can have a rectangular shape. In that regard, the vertical wall can comprise four vertical walls that define an outer boundary of the rectangular shape. In accordance with an example embodiment, two of the vertical walls can have a length of 12.8 centimeters (cm) and a height of 1.42 cm, and the other two vertical walls can have a length of 8.55 cm and a height of 1.42 cm. In another respect, cell culture plate 120 can have a circular shape. Other examples of the defined shape cell culture plate 120 can take or other examples of vertical wall dimensions are also possible.

The distance 118 between the optical filter 114 and the second lens 116 and the distance 122 between the optical filter 114 and the cell culture plate 120 may be selected to uniformly irradiate the cell culture plate 120. "Uniformly irradiate" and "uniform irradiation" refers to providing light dispersed by the second lens 116 to the entire area of the cell culture plate 120 or to the entire bottom area of the cell culture plate 120.

The distance 118 between the optical filter 114 and the second lens 116 to uniformly irradiate the cell culture plate 120 may be 13.6 cm. Other distances between the optical filter 114 and the second lens 116 to uniformly irradiate the cell culture plate 120 are possible. The distance 118 can be a distance between portions of optical filter 114 and second lens 116 that are nearest each other. With respect to the orientation of lighting system 100 in FIG. 1, those portions can include a lower side of optical filter 114 and an upper side of second lens 116. Alternatively, the distance 118 between the optical filter 114 and the second lens 116 may be a distance between a vertical center point of the optical filter 114 and a vertical center point of the second lens 116. Other examples of specifying the distance 118 between the optical filter 114 and the second lens 116 are possible.

The distance 122 between the optical filter 114 and the cell culture plate 120 to uniformly irradiate the cell culture plate 120 can be specified in various ways. In one respect, the distance 122 can be specified as a distance from a highest point of optical filter 114 to the external surface of the bottom area of the cell culture plate 120. In that regard, for a first case, the distance 122 can be 95.5 cm. In another respect, the distance 122 can be specified as a distance from the highest point of optical filter 114 to the top area of the cell culture plate 120. In accordance with the first case referred to above, if the vertical wall (the distance between the top area of cell culture plate 120 and the external surface of the bottom area of the cell culture plate 120) has a height of 1.42 cm, then the distance can be 94.08 cm. In another respect, the distance 122 between the optical filter 114 and the cell culture plate 120 may be specified as a distance between a closest point of the optical filter 114 and a closest point of the cell culture plate 120. In yet another respect, the distance 122 between the optical filter 114 and the cell culture plate 120 may be specified as a distance between a vertical center point of the optical filter 114 and a vertical center point of the cell culture plate 120. Other examples of specifying the distance 122 between the optical filter 114 and the cell culture plate 120 are possible.

The components connected together in the lighting system 100, or in other lighting systems described herein, can be removably connected such that the components can be disconnected from one another and removed from the lighting system for adjustment, cleaning, repair, replacement or otherwise. The portions of components that connect to one another can include one or more seals to prevent, or at least reduce, any light from exiting the lighting system at those connected portions. A person skilled in the art will understand that the connection of two or more components can be facilitated by use of one or more spacers to achieve desired distances between components of the lighting system. One or more spacers may be placed between components of the lighting system so as not to impact uniform irradiation of the cell culture plate. For clarity of the figures, spacers are typically not shown.

In an alternative embodiment, the light-port 106 is connected to the infrared absorbing filter 110. With this arrangement, the infrared absorbing filter 110 is connected to the first lens 108, and the first lens 108 is connected to the reflector 112.

In another embodiment, the first lens 108 is outside of the light-port 106. With this arrangement, the light-port 106 may be connected to the first lens 108, the first lens 108 may be connected to the infrared absorbing filter 110, and the infrared absorbing filter 110 may be connected to the reflector 112. Alternatively, the light-port 106 may be connected to the infrared absorbing filter 110, the infrared absorbing filter 110 may be connected to the first lens 108, and the first lens 108 may be connected to the reflector 112.

In another embodiment, the lamp housing 102, the first lens 108, the infrared absorbing filter 110, the reflector 112, the optical filter 114, and the second lens 116 are each positioned on a ledge (not shown) above a table (not shown). With this arrangement, the cell culture plate 120 is then positioned on a temperature controlling device (not shown) located on the table. The temperature controlling device can be arranged in various configurations. For instance, the temperature controlling device may be a heating device or a cooling device. The temperature controlling device may maintain the cell culture plate 120, as well as the contents of the cell culture plate 120, at a regulated temperature.

In yet another embodiment, the reflector 112 is inverted. With this arrangement, the reflector 112 reflects the first portion of the collimated broad spectrum light upward. As such, the optical filter 114, the second lens 116, and the cell culture plate 120 are each located above the reflector 112. In accordance with this embodiment, uniform irradiation of the cell culture plate 120 comprises providing light dispersed by the second lens 116 to the entire bottom area of the cell culture plate 120.

FIG. 2 illustrates an alternative embodiment lighting system generally designated 200 and components thereof. The lighting system 200 includes a lamp housing 202, a first lens 208, an infrared absorbing filter 210, a reflector 212, an optical filter 214, a second lens 216, a cell culture plate 220, a ring stand 224, a first support ring 226, and a base 228. The lamp housing 202 includes a lamp 204, a mirror 205, and a light-port 206.

In the lighting system 200, the first lens 208 is within the light-port 206. The infrared absorbing filter 210 is connected to the light-port 206. The reflector 212 is connected to the infrared absorbing filter 210. The optical filter 214 is connected to the reflector 212. The second lens 216 is supported by the first support ring 226. Support for the second lens 216 by the first support ring 226 may include the second lens 216 being on the first support ring 226. The first support ring 226 is removably attached to the ring stand 224. The second lens 216 is located a distance 218 from the optical filter 214. The first support ring 226 may be slid up the ring stand 224 to adjust the distance 218 between the optical filter 214 and the second lens 216. The first support ring 226 may be slid down the ring stand 224 to adjust the distance 218 between the optical filter 214 and the second lens 216. The base 228 is connected to the ring stand 224. The cell culture plate 220 is located a distance 222 from the optical filter 214.

Components of the lighting system 200 can be arranged like components of the lighting system 100 illustrated in FIG. 1. For example, the lamp housing 202 can be arranged like the lamp housing 102, the lamp 204 can be arranged like the lamp 104, the light-port 206 can be arranged like the light-port 106, the first lens 208 can be arranged like the first lens 108, the infrared absorbing filter 210 can be arranged like the infrared absorbing filter 110, the reflector 212 can be arranged like the reflector 112, the optical filter 214 can be arranged like the optical filter 114, the second lens 216 can be arranged like the second lens 116, and the cell culture plate 220 can be arranged like the cell culture plate 120.

In operation, the cell culture plate 220, as well as the contents of the cell culture plate 220, is irradiated with light from the lamp 204. First, broad spectrum light from the lamp 204 exits the lamp housing 202 by passing through the light-port 206. The broad spectrum light may be reflected by the mirror 205 to the light-port 206. Something other than a mirror could be used to reflect the broad spectrum light to the light-port 206. For simplicity of describing the lighting system 200, and other lighting systems described herein, the component that reflects the broad spectrum light to the light-port 206 can be referred to as a mirror. The mirror 205 may be one or more concave mirrors. With this arrangement, the mirror 205 may increase the power of the broad spectrum light passing through the light-port 206. Additionally, the mirror 205 may have two or more adjustments (not shown) to allow the mirror 205 to move in perpendicular planes. The two or more adjustments can be used to optimize the broad spectrum light for irradiating the cell culture plate 220. For instance, the two or more adjustments can be used to center the broad spectrum light through the first lens 208. As another example, the two or more adjustments can be used to avoid passing a most intense portion of the broad spectrum light through an arc of one or more electrodes associated with the lamp 204.

After the broad spectrum light exits the lamp housing 202 by passing through the light-port 206, the broad spectrum light is collimated by the first lens 208.

After the broad spectrum light is collimated by the first lens 208, the collimated broad spectrum light reaches the infrared absorbing filter 210. The infrared absorbing filter 210 absorbs infrared light of the collimated broad spectrum light. The infrared absorbing filter 210 also passes a first portion of the collimated broad spectrum light to the reflector 212.

After the first portion of the collimated broad spectrum light is passed by the infrared absorbing filter 210 to the reflector 212, the reflector 212 reflects the first portion of the collimated broad spectrum light. The first portion of the collimated broad spectrum light then propagates to the optical filter 214. Alternatively, the reflector 212 may reflect only a portion of the first portion of the collimated broad spectrum light, and the portion of the first portion of the collimated broad spectrum light then propagates to the optical filter 214. The reflector 212 reflects light with the same given range of wavelengths as the reflector 110.

After the first portion of the collimated broad spectrum light propagates to the optical filter 214, the optical filter 214 passes a second portion of the collimated broad spectrum light to the second lens 216. The optical filter 214 passes light with the same given range of wavelengths as the optical filter 114.

After the second portion of the collimated broad spectrum light is passed by the optical filter 214 to the second lens 216, the second lens 216 disperses the second portion of the collimated broad spectrum light to the cell culture plate 220.

The distance 218 between the optical filter 214 and the second lens 216 and the distance 222 between the optical filter 214 and the cell culture plate 220 may be selected to uniformly irradiate the cell culture plate 220. "Uniformly irradiate" and "uniform irradiation" refers to providing light dispersed by the second lens 216 to the entire area of the cell culture plate 220 or to the entire bottom area of the cell culture plate 220.

The distance 218 between the optical filter 214 and the second lens 216 to uniformly irradiate the cell culture plate 220 may be 13.6 cm. Other distances between the optical filter 214 and the second lens 216 to uniformly irradiate the cell culture plate 220 are possible. The distance 218 can be a distance between portions of optical filter 214 and second lens 216 that are nearest each other. With respect to the orientation of lighting system 200 in FIG. 2, those portions can include a lower side of optical filter 214 and an upper side of second lens 216. Alternatively, the distance 218 between the optical filter 214 and the second lens 216 may be a distance between a vertical center point of the optical filter 214 and a vertical center point of the second lens 216. Other examples of specifying the distance 218 between the optical filter 214 and the second lens 216 are possible.

The distance 222 between the optical filter 214 and the cell culture plate 220 to uniformly irradiate the cell culture plate 220 can be specified in various ways. In one respect, the distance 222 can be specified as a distance from a highest point of optical filter 214 to the external surface of the bottom area of the cell culture plate 220. In that regard, for a first case, the distance 222 can be 95.5 cm. In another respect, the distance 222 can be specified as a distance from the highest point of optical filter 214 to the top area of the cell culture plate 220. In accordance with the first case referred to above, if the vertical wall (the distance between the top area of cell culture plate 220 and the external surface of the bottom area of the cell culture plate 220) has a height of 1.42 cm, then the distance can be 94.08 cm. In another respect, the distance 222 between the optical filter 214 and the cell culture plate 220 may be specified as a distance between a closest point of the optical filter 214 and a closest point of the cell culture plate 220. In yet another respect, the distance 222 between the optical filter 214 and the cell culture plate 220 may be specified as a distance between a vertical center point of the optical filter 214 and a vertical center point of the cell culture plate 220. Other examples of specifying the distance 222 between the optical filter 214 and the cell culture plate 220 are possible.

In an alternative embodiment, the light-port 206 is connected to the infrared absorbing filter 210. With this arrangement, the infrared absorbing filter 210 is connected to the first lens 208, and the first lens 208 is connected to the reflector 212.

In another embodiment, the first lens 208 is outside of the light-port 206. With this arrangement, the light-port 206 may be connected to the first lens 208, the first lens 208 may be connected to the infrared absorbing filter 210, and the infrared absorbing filter 210 may be connected to the reflector 212. Alternatively, the light-port 206 may be connected to the infrared absorbing filter 210, the infrared absorbing filter 210 may be connected to the first lens 208, and the first lens 208 may be connected to the reflector 212.

In yet another embodiment, the lamp housing 202, the first lens 208, the infrared absorbing filter 210, the reflector 212, the optical filter 214, and the second lens 216 are each positioned on a ledge (not shown) above a table (not shown). With this arrangement, the cell culture plate 220 may then be positioned on a temperature controlling device (not shown) located on the table. The temperature controlling device can be arranged in various configurations. For instance, the temperature controlling device may be a heating device or a cooling device. The temperature controlling device may maintain the cell culture plate 220, as well as the contents of the cell culture plate 220, at a regulated temperature.

Although FIG. 2 illustrates the cell culture plate 220 on one side of base 228, in an alternative arrangement, the base 228 may be rotated about a vertical axis of ring stand 224 such that base 228 is positioned where the cell culture plate 220 is shown in FIG. 2 and cell culture plate 220 can be placed upon base 228. In yet another alternative arrangement, the ring stand 224 may be positioned in a center of the base 228 and cell culture plate 220 is placed upon a portion of the base 228 below the first support ring 226.

FIG. 3 illustrates another embodiment of a lighting system generally designated 300 and components thereof. The lighting system 300 includes a lamp housing 302, a first lens 312, an infrared absorbing filter 314, an optical filter 316, a second lens 318, a cell culture plate 322, a ring stand 326, a base 328, and a first support ring 330. The lamp housing 302 includes a lamp 304, a light-port 306, a top 308, and a bottom 310.

In the lighting system 300, the lamp 304 is within the lamp housing 302. The light-port 306 is within the bottom 310. The infrared absorbing filter 314, the optical filter 316, and the second lens 318 are located at positions below the bottom 310. The first lens 312 is within the light-port 306. The infrared absorbing filter 314 is connected to the light-port 306. The optical filter 316 is connected to the infrared absorbing filter 314. The second lens 318 is supported by the first support ring 330. Support for the second lens 318 by the first support ring 330 may include the second lens 318 being on the first support ring 330. The first support ring 330 is removably attached to the ring stand 326. The second lens is located a distance 320 from the optical filter 316. The first support ring 330 may be slid up the ring stand 326 to adjust the distance 320 between the optical filter 316 and the second lens 312. The first support ring 330 may be slid down the ring stand 326 to adjust the distance 320 between the optical filter 316 and the second lens 318. The base 328 is connected to the ring stand 326. The cell culture plate 322 is located a distance 324 from the optical filter 316.

Components of the lighting system 300 can be arranged like components of the lighting system 100 illustrated in FIG. 1. For example, the lamp housing 302 can be arranged like the lamp housing 102, the lamp 304 can be arranged like the lamp 104, the light-port 306 can be arranged like the light-port 106, the first lens 312 can be arranged like the first lens 108, the infrared absorbing filter 314 can be arranged like the infrared absorbing filter 110, the optical filter 314 can be arranged like the optical filter 114, the second lens 318 can be arranged like the second lens 116, and the cell culture plate 322 can be arranged like the cell culture plate 120.

In operation, the cell culture plate 322, as well as the contents of the cell culture plate 322, is irradiated with light from the lamp 304. First, broad spectrum light from the lamp 304 exits the lamp housing 302 by passing through the light-port 306.

After the broad spectrum light exits the lamp housing 302 by passing through the light-port 306, the broad spectrum light is collimated by the first lens 312.

After the broad spectrum light is collimated by the first lens 312, the collimated broad spectrum light reaches the infrared absorbing filter 314. The infrared absorbing filter 314 absorbs infrared light of the collimated broad spectrum light. The infrared absorbing filter 314 also passes a first portion of the collimated broad spectrum light to the optical filter 316.

After the first portion of the collimated broad spectrum light is passed by the infrared absorbing filter 314 to the optical filter 316, the optical filter 316 passes a second portion of the collimated broad spectrum light to the second lens 318. As an example, the light passed to the second lens 318 may be collimated light within the range of 400 nm to 630 nm (i.e., no infrared or ultraviolet light). Narrower band-pass filters can be used to reduce the range.

After the second portion of the collimated broad spectrum light is passed by the optical filter 316 to the second lens 318, the second lens 318 disperses the second portion of the collimated broad spectrum light to the cell culture plate 322.

The distance 320 between the optical filter 316 and the second lens 318 and the distance 324 between the optical filter 316 and the cell culture plate 322 may be selected to uniformly irradiate the cell culture plate 322. "Uniformly irradiate" and "uniform irradiation" refers to providing light dispersed by the second lens 318 to the entire area of the cell culture plate 322 or to the entire bottom area of the cell culture plate 322.

The distance 320 between the optical filter 316 and the second lens 318 to uniformly irradiate the cell culture plate 322 may be 13.6 cm. Other distances between the optical filter 316 and the second lens 318 to uniformly irradiate the cell culture plate 322 are possible. The distance 320 can be a distance between portions of optical filter 316 and second lens 318 that are nearest each other. With respect to the orientation of lighting system 300 in FIG. 3, those portions can include a lower side of optical filter 316 and an upper side of second lens 318. Alternatively, the distance 320 between the optical filter 316 and the second lens 318 may be a distance between a vertical center point of the optical filter 316 and a vertical center point of the second lens 318. Other examples of specifying the distance 320 between the optical filter 316 and the second lens 318 are possible.

The distance 324 between the optical filter 316 and the cell culture plate 322 to uniformly irradiate the cell culture plate 322 can be specified in various ways. In one respect, the distance 324 can be specified as a distance from a highest point of optical filter 316 to the external surface of the bottom area of the cell culture plate 322. In that regard, for a first case, the distance 324 can be 95.5 cm. In another respect, the distance 324 can be specified as a distance from the highest point of optical filter 316 to the top area of the cell culture plate 322. In accordance with the first case referred to above, if the vertical wall (the distance between the top area of cell culture plate 322 and the external surface of the bottom area of the cell culture plate) has a height of 1.42 cm, then the distance can be 94.08 cm. In another respect, the distance 324 between the optical filter 316 and the cell culture plate 322 may be specified as a distance between a closest point of the optical filter 316 and a closest point of the cell culture plate 322. In yet another respect, the distance 324 between the optical filter 316 and the cell culture plate 322 may be specified as a distance between a vertical center point of the optical filter 316 and a vertical center point of the cell culture plate 322. Other examples of specifying the distance 324 between the optical filter 316 and the cell culture plate 322 are possible.

In an alternative embodiment, the first lens 312 is outside of the light-port 306. With this arrangement, the light-port 306 may be connected to the first lens 312, and the first lens 312 may be connected to the infrared absorbing filter 314. Alternatively, the light-port 306 may be connected to the infrared absorbing filter 314, and the infrared absorbing filter 314 may be connected to the first lens 312.

In another embodiment, the light-port 306 may be connected to the infrared absorbing filter 314. With this arrangement, the infrared absorbing filter 314 is connected to the first lens 312, and the first lens 312 is connected to the optical filter 316.

In yet another embodiment, the lamp housing 302, the first lens 312, the infrared absorbing filter 314, the optical filter 316, and the second lens 318 are each positioned on a ledge (not shown) above a table (not shown). With this arrangement, the cell culture plate 322 is then be positioned on a temperature controlling device (not shown) located on the table. The temperature controlling device can be arranged in various configurations. For instance, the temperature controlling device may be a heating device or a cooling device. The temperature controlling device may maintain the cell culture plate 322, as well as the contents of the cell culture plate 322, at a regulated temperature.

Although FIG. 3 illustrates the cell culture plate 322 on one side of base 328, in an alternative arrangement, the base 328 may be rotated about a vertical axis of ring stand 326 such that base 328 is positioned where the cell culture plate 322 is shown in FIG. 3 and cell culture plate 322 can be placed upon base 328. In yet another alternative arrangement, the ring stand 326 may be positioned in a center of the base 328 and cell culture plate 322 is placed upon a portion of the base 328 below the first support ring 330.

Figure 4:
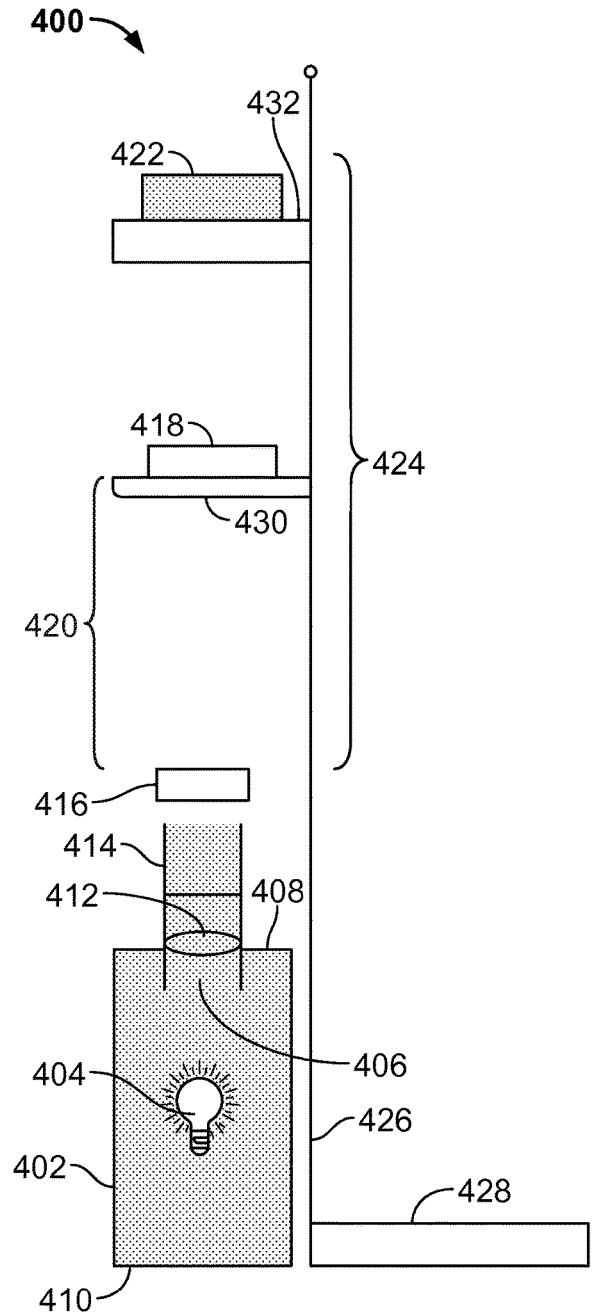
FIG. 4 is a block diagram of another embodiment lighting system.

FIG. 4 illustrates another embodiment of a lighting system generally designated 400 and components thereof. The lighting system 400 includes a lamp housing 402, a first lens 412, an infrared absorbing filter 414, an optical filter 416, a second lens 418, a cell culture plate 422, a ring stand 426, a base 428, a first support ring 430, and a second support ring 432. The lamp housing 402 includes a lamp 404, a light-port 406, a top 408, and a bottom 410.

In the lighting system 400, the lamp 404 is within the lamp housing 402. The light-port 406 is within the top 408. The infrared absorbing filter 414, the optical filter 416, and the second lens 418 are located at positions above the top 408. The first lens 412 is within the light-port 406. The infrared absorbing filter 414 is connected to the light-port 406. The optical filter 416 is connected to the infrared absorbing filter 414. The second lens 418 is supported by the first support ring 430. Support for the second lens 418 by the first support ring 430 may include the second lens 418 being on the first support ring 430. The first support ring 430 is removably attached to the ring stand 426. The second lens is located a distance 420 from the optical filter 416. The cell culture plate 422 is supported by the second support ring 432. Support for the cell culture plate 422 by the second support ring 432 may include the cell culture plate 422 being on the second support ring 432. The second support ring 432 is removably attached to the ring stand 426. The cell culture plate 422 is located a distance 424 from the optical filter 416. The base 428 is connected to the ring stand 426. The first support ring 430 may be slid up the ring stand 426 to adjust the distance 420 between the optical filter 414 and the second lens 418. The first support ring 430 may be slid down the ring stand 426 to adjust the distance 420 between the optical filter 416 and the second lens 418. The second support ring 432 may be slid up the ring stand 426 to adjust the distance 424 between the optical filter 414 and the cell culture plate 422. The second support ring 432 may be slid down the ring stand 426 to adjust the distance 424 between the optical filter 416 and the cell culture plate 422.

Components of the lighting system 400 can be arranged like components of the lighting system 100 illustrated in FIG. 1. For example, the lamp housing 402 can be arranged like the lamp housing 102, the lamp 404 can be arranged like the lamp 104, the light-port 406 can be arranged like the light-port 106, the first lens 412 can be arranged like the first lens 108, the infrared absorbing filter 414 can be arranged like the infrared absorbing filter 110, the optical filter 416 can be arranged like the optical filter 114, the second lens 418 can be arranged like the second lens 116, and the cell culture plate 422 can be arranged like the cell culture plate 120, except that the cell culture plate 422 comprises multiple wells each with a clear bottom but otherwise black opaque.

In operation, the cell culture plate 422, as well as the contents of the cell culture plate 422, is irradiated with light from the lamp 404. First, broad spectrum light from the lamp 404 exits the lamp 404 by passing through the light-port 406.

After the broad spectrum light exits the lamp housing 402 by passing through light-port 406, the broad spectrum light is collimated by the first lens 412.

After the broad spectrum light is collimated by the first lens 412, the collimated broad spectrum light reaches the infrared absorbing filter 414. The infrared absorbing filter 414 absorbs infrared light of the collimated broad spectrum light. The infrared absorbing filter 414 also passes a first portion of the collimated broad spectrum light to the optical filter 416.

After the first portion of the collimated broad spectrum light is passed by the infrared absorbing filter 414 to the optical filter 416, the optical filter 416 passes a second portion of the collimated broad spectrum light to the second lens 418. As an example, the light passed to the second lens 318 may be collimated light within the range of 400 nm to 630 nm (i.e., no infrared or ultraviolet light). Narrower band-pass filters can be used to reduce the range.

After the second portion of the broad spectrum light is passed by the optical filter 416 to the second lens 418, the second lens 418 disperses the second portion of the collimated broad spectrum light to the cell culture plate 422.

The distance 420 between the optical filter 416 and the second lens 418 and the distance 424 between the optical filter 416 and cell culture plate 422 may be selected to uniformly irradiate the cell culture plate 422. "Uniformly irradiate" and "uniform irradiation" refers to providing light dispersed by the second lens 416 to the entire area of the cell culture plate 422 or to the entire bottom area of the cell culture plate 422.

The distance 420 between the optical filter 416 and the second lens 418 to uniformly irradiate the cell culture plate 422 may be 13.6 cm. Other distances between the optical filter 416 and the second lens 418 to uniformly irradiate the cell culture plate 422 are possible. The distance 420 can be a distance between portions of optical filter 416 and second lens 418 that are nearest each other. With respect to the orientation of lighting system 400 in FIG. 4, those portions can include an upper side of optical filter 416 and a lower side of second lens 418. Alternatively, the distance 420 between the optical filter 416 and the second lens 418 may be a distance between a vertical center point of the optical filter 416 and a vertical center point of the second lens 418. Other examples of specifying the distance 420 between the optical filter 416 and the second lens 418 are possible.

The distance 424 between the optical filter 416 and the cell culture plate 422 to uniformly irradiate the cell culture plate 422 can be specified in various ways. In one respect, the distance 424 can be specified as a distance from a highest point of the optical filter 416 to the external surface of the bottom area of the cell culture plate 422. In that regard, for a first case, the distance 424 can be 95.5 cm. In another respect, the distance 424 can be specified as a distance from the highest point of optical filter 416 to the top area of the cell culture plate 422. In accordance with the first case referred to above, if the vertical wall (the distance between the top area of cell culture plate 422 and the external surface of the bottom area of the cell culture plate 422) has a height of 1.42 cm, then the distance can be 94.08 cm. In another respect, the distance 424 between the optical filter 416 and the cell culture plate 422 may be specified as a distance between a closest point of the optical filter 416 and a closest point of the cell culture plate 422. In yet another respect, the distance 424 between the optical filter 416 and the cell culture plate 422 may be specified as a distance between a vertical center point of the optical filter 416 and a vertical center point of the cell culture plate 422. Other examples of specifying the distance 424 between the optical filter 416 and the cell culture plate 422 are possible.

In an alternative embodiment, the first lens 412 is outside of the light-port 406. With this arrangement, the light-port 406 may be connected to the first lens 412, and the first lens 412 may be connected to the infrared absorbing filter 414. Alternatively, the light-port 406 may be connected to the infrared absorbing filter 414, and the infrared absorbing filter 414 may be connected to the first lens 412.

In another embodiment, the light-port 406 may be connected to the infrared absorbing filter 414. With this arrangement, the infrared absorbing filter 414 is connected to the first lens 412, and the first lens 412 is connected to the optical filter 416.

In yet another embodiment, the lamp housing 402, the first lens 412, the infrared absorbing filter 414, the optical filter 416, and the second lens 418 are each positioned on a ledge (not shown) above a table (not shown). With this arrangement, the cell culture plate 422 may then be positioned on a temperature controlling device (not shown) located on the table. The temperature controlling device can be arranged in various configurations. For instance, the temperature controlling device may be a heating device or a cooling device. The temperature controlling device may maintain the cell culture plate 422, as well as the contents of the cell culture plate 422, at a regulated temperature.

For simplicity of the block diagrams of FIGS. 1-4, the means for connecting optical filters 114, 214, 316, and 416 to reflectors 112 and 212 and to infrared absorbing filters 314 and 414, respectively are not shown. As an example, those means can be similar to the means shown in FIG. 5 to connect an infrared blocking filter 526 to a reflector 524.

Figure 5:
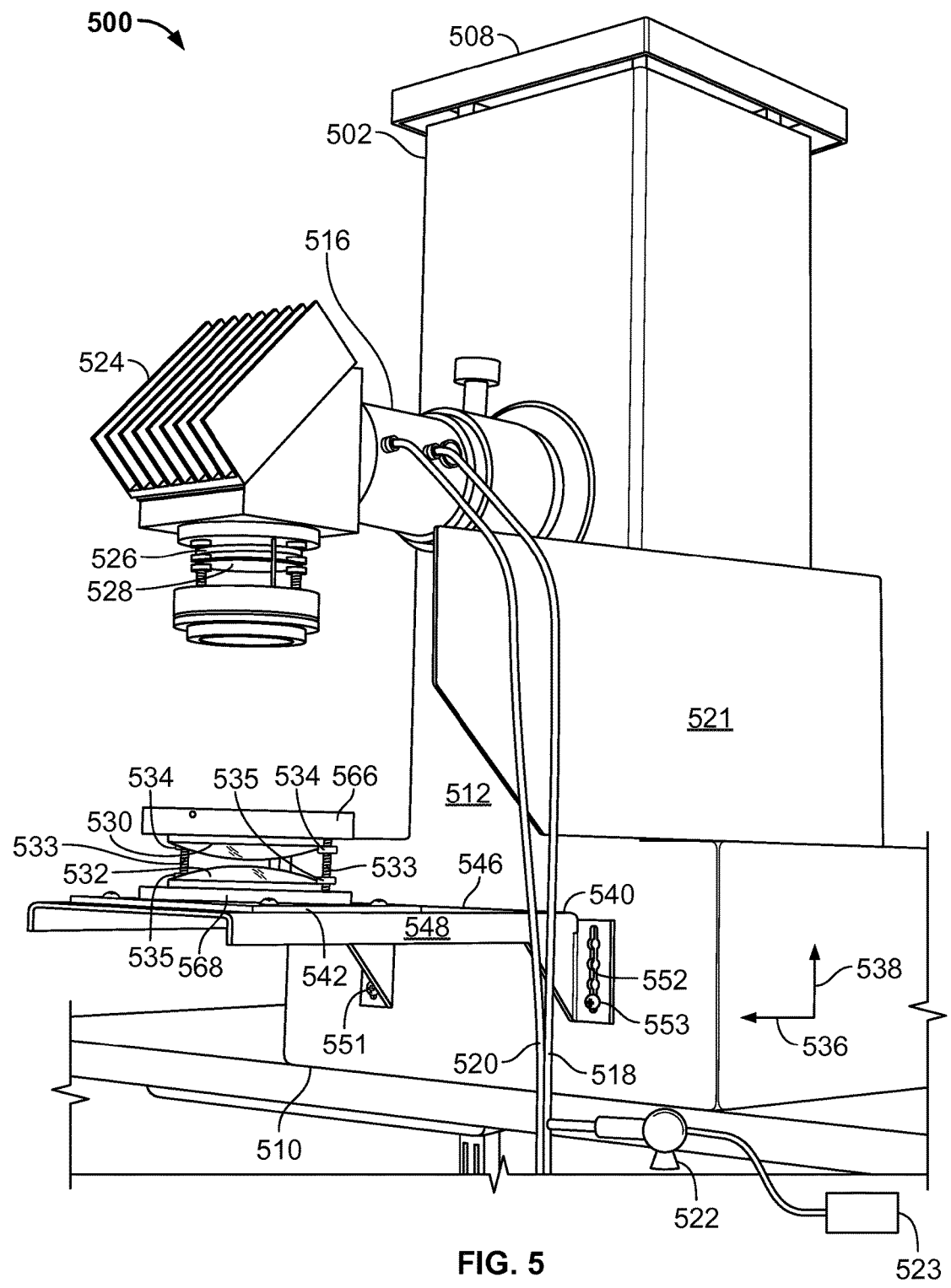
FIG. 5 is a perspective view of another embodiment lighting system.
Figure 6:
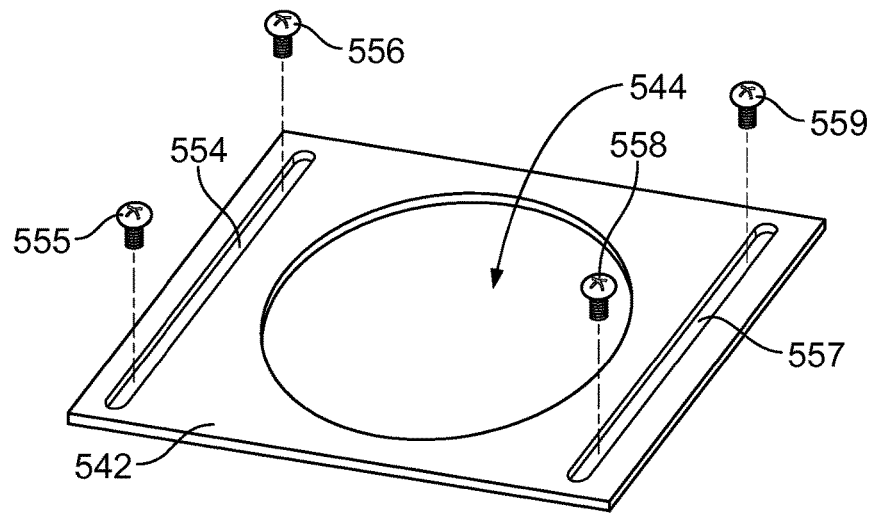
FIG. 6 is a perspective view of the lens slider and related components of the lighting system illustrated in FIG. 5.
Figure 7:
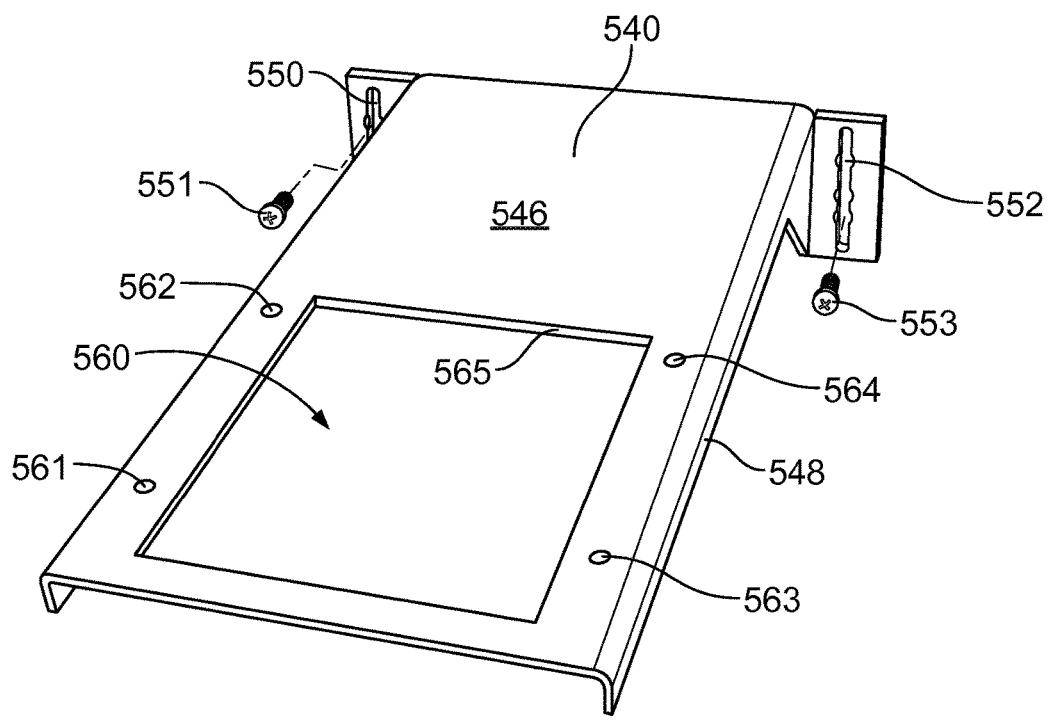
FIG. 7 is a perspective view of the shelf and related components of the lighting system illustrated in FIG. 5.

FIGS. 5-7 illustrate another embodiment of a lighting system 500 and components thereof. The lighting system 500 includes a lamp housing 502, a first lens (not shown), an infrared absorbing liquid filter 516, an inlet cooling tube 518, an outlet cooling tube 520, a supporting member 521, a pump 522, a cooling system 523, a reflector 524, an infrared blocking filter 526, a short pass filter 528, a first dispersing lens 530, a first dispersing lens holder 566, a second dispersing lens 532, a second dispersing lens holder 568, an adjustment rod 533, a first adjustment spacer 534, a second adjustment spacer 535, a shelf 540, a lens slider 542, and a cell culture plate (not shown). The lamp housing 502 includes a lamp (not shown), a mirror (not shown), a light-port (not shown), a top 508, a bottom 510, and a wall 512. The shelf 540 includes a shelf top 546, a shelf riser 548, a first parallel adjustment slot 550, a first parallel adjustment fastener 551, a second parallel adjustment slot 552, a second parallel adjustment fastener 553, a second hole 560 for passing light, a first lens slider attachment 561, a second lens slider attachment 562, a third lens slider attachment 563, a fourth lens slider attachment 564, and a race 565. The lens slider 542 includes a first hole 544 for passing light, a first perpendicular adjustment slot 554, a first perpendicular adjustment fastener 555, a second perpendicular adjustment fastener 556, a second perpendicular adjustment slot 557, a third perpendicular adjustment fastener 558, and a fourth perpendicular adjustment fastener 559.

In the lighting system 500, the lamp is within the lamp housing like the lamps in the lighting systems illustrated in FIGS. 1-4. The light-port is within the lamp housing 502 like the light-ports in the lighting systems illustrated in FIGS. 1-4. The mirror can be arranged like the mirror 205 of the lighting system 200 illustrated in FIG. 2. The first lens is within the light-port like the first lenses in the lighting systems illustrated in FIGS. 1-4. The first lens, the infrared absorbing liquid filter 516, the reflector 524, the infrared blocking filter 526, and the short pass filter 528 are each located at positions between the top 508 and the bottom 510. The bottom 510 can be metal. The cell culture plate can be arranged like the cell culture plate 120 in the lighting system 100 illustrated in FIG. 1.

Additionally, in the lighting system 500, the infrared absorbing liquid filter 516 is connected to the light-port like the infrared absorbing filters are connected to the light-ports in the lighting systems illustrated in FIGS. 1-4. The infrared absorbing liquid filter 516 is connected to the inlet cooling tube 518. The inlet cooling tube 518 is supported by the supporting member 521. The inlet cooling tube 518 is connected to the pump 522. The pump 522 is connected to the cooling system 523. The connection can be in-line. The infrared absorbing liquid filter 516 is connected to the outlet cooling tube 520. The outlet cooling tube 520 is supported by the supporting member 521. The outlet cooling tube 520 is connected to the pump 522.

Additionally, in the lighting system 500, the reflector 524 is connected to the infrared absorbing liquid filter 516. The infrared blocking filter 526 is connected to the reflector 524. The short pass filter 528 is connected to the infrared blocking filter 526. The first dispersing lens 530 is located a distance from the short pass filter 528 like the second lenses are located a distance from the optical filters in the lighting systems illustrated in FIGS. 1-4. The first dispersing lens 530 is supported by the first dispersing lens holder 566. The first dispersing lens 530 is adjacent to the second dispersing lens 532 with a gap between the first dispersing lens 530 and the second dispersing lens 532. The gap between the first dispersing lens 530 and the second dispersing lens 532 is adjustable by the adjustment rod 533, the first adjustment spacer 534, and the second adjustment spacer 535. Two adjustment rods 533 each with the first adjustment spacer 534 and the second adjustment spacer 535 are shown in FIG.

5 and can be sufficient to adjust the gap between the first dispersing lens 530 and the second dispersing lens 532. In some embodiments, three or more adjustment rods 533 each with the first adjustment spacer 534 and the second adjustment spacer 535 equally spaced around the first dispersing lens 530 and the second dispersing lens 532 are possible. The second dispersing lens 532 is supported by the second dispersing lens holder 568. The second dispersing lens holder 568 is removably attached to the lens slider 542. More specifically, the second dispersing lens holder 568 has a flange (not shown) that rests on the lens slider 542. A portion of the second dispersing lens holder 568 can be positioned within the first hole 544 for passing light or within the first hole 544 and the second hole 560 for passing light. Alternatively, a portion of the second dispersing lens holder 568 can extend beyond the first hole 544 for passing light and the second hole 560 for passing light. The lens slider 542 is removably attached to shelf top 546. The shelf top 546 is located in a direction perpendicular 536 to the wall 512. The shelf riser 548 is located in a direction parallel 538 to the wall 512.

Additionally, in the lighting system 500, a position of the first dispersing lens 530 and the second dispersing lens 532 in the direction perpendicular 536 to the wall 512 is adjustable by the first perpendicular adjustment slot 554, the first perpendicular adjustment fastener 555, the second perpendicular adjustment fastener 556, the second perpendicular adjustment slot 557, the third perpendicular adjustment fastener 558, and the fourth perpendicular adjustment fastener 559. A position of the first dispersing lens 530 and the second dispersing lens 532 in the direction parallel 538 to the wall 512 is adjustable by the first parallel adjustment slot 550, the first parallel adjustment fastener 551, the second parallel adjustment slot 552, and the second parallel adjustment fastener 553.

In operation, the cell culture plate, as well as the contents of the cell culture plate, is irradiated with light from the lamp. The lamp housing 502 may be Oriel® Instruments Model No. 66921 sold by Newport Corporation. First, broad spectrum light from the lamp exits the lamp by passing through the light-port. The lamp may be a 1000 watt xenon short arc lamp. The 1000 watt xenon short arc lamp may be Oriel® Instruments Model No. 6271 sold by Newport Corporation. The broad spectrum light may be reflected by the mirror to the light-port. With this arrangement, the mirror may increase the power of the broad spectrum light passing through the light-port. Additionally, the mirror may have two or more adjustments (not shown) to allow the mirror to move in perpendicular planes. The two or more adjustments can be used to optimize the broad spectrum light for irradiating the cell culture plate. For instance, the two or more adjustments can be used to center the broad spectrum light through the first lens. As another example, the two or more adjustments can be used to avoid passing a most intense portion of the broad spectrum light through an arc of one or more electrodes associated with the lamp. The lamp housing 502 may be sealed so that the broad spectrum light from the lamp exits the lamp housing 502 only through the light-port. Alternatively, the lamp housing 502 may be sealed so that less than 1% of the broad spectrum light from the lamp exits the lamp housing 502 other than through the light-port.

After the broad spectrum light exits the lamp housing 502 by passing through the light-port, the broad spectrum light is collimated by the first lens. The first lens can be arranged in various configurations. In a first configuration, the first lens may be a 50 mm focal length condenser lens. In that first configuration or in another configuration, the first lens may be a Fresnel lens. Moreover, in that first configuration or in another configuration, the first lens may have a diameter of 2 or 3 in. Other examples of the diameter of the first lens are possible. In a second example configuration, the first lens can comprise two or more lenses. In accordance with one or more of these example embodiments of the first lens, the first lens can comprise a lens holder configured for supporting a lens, such as a glass lens, and for connecting the first lens to another component of the lighting system 500, such as infrared absorbing liquid filter 516, the light-port, the reflector 524, or a spacer.

After the broad spectrum light is collimated by the first lens, the collimated broad spectrum light reaches the infrared absorbing liquid filter 516. The infrared absorbing liquid filter 516 may be Oriel® Instruments Model No. 6123 sold by Newport Corporation. The infrared absorbing liquid filter 516 absorbs infrared light of the collimated broad spectrum light. The infrared absorbing liquid filter 516 may absorb between 90% and 100%, inclusive, of the infrared light of the collimated broad spectrum light. Other infrared absorbing ranges of the infrared absorbing liquid filter 516 are possible. The temperature of the infrared absorbing liquid filter 516 may be controlled by pumping a cooling fluid to a jacket (not shown) of the infrared absorbing liquid filter 516 at a flow rate through the inlet cooling tube 518 and the outlet cooling tube 520 using the pump 522. The cooling fluid may be ice-cold water. The cooling fluid may be cooled by the cooling system 523. The flow rate may be 6 milliliters per minute (mL/min). The pump 522 may be a peristaltic pump. The infrared absorbing liquid filter 516 also passes a first portion of the collimated broad spectrum light to the reflector 524.

After the first portion of the collimated broad spectrum light is passed by the infrared absorbing liquid filter 516 to the reflector 524, the reflector 524 reflects the first portion of the collimated broad spectrum light. The first portion of the collimated broad spectrum light then propagates to the infrared blocking filter 526. Alternatively, the reflector 524 may reflect only a portion of the first portion of the collimated broad spectrum light, and the portion of the first portion of the collimated broad spectrum light then propagates to the infrared blocking filter 526. The reflector 524 can be arranged in a variety of configurations. In a first configuration, the reflector 524 may be a beam turning dichroic mirror. The reflector 524 may be Oriel® Instruments Model No. 66229 sold by Newport Corporation. In that first configuration or another configuration, the reflector 524 may have a 2.0 in diameter. Other diameters for the reflector 524 are possible. In a second configuration, the reflector 524 may be two or more beam turning dichroic mirrors. The first portion of the collimated broad spectrum light that is reflected by the reflector 524 to the infrared blocking filter 526 may have a wavelength in a given range. For example, the collimated broad spectrum light may have a given range of 400 nm to 700 nm. Other given ranges are possible. In some embodiments, the reflector 524 absorbs at least a portion of infrared light or at least a portion of ultraviolet light of the collimated broad spectrum light. With this arrangement, the reflector 524 functions like an optical filter by passing only visible light to the infrared blocking filter 526.

After the first portion of the collimated broad spectrum light propagates to the infrared blocking filter 526, the infrared blocking filter 526 absorbs residual infrared light of the first portion of the collimated broad spectrum light. The infrared blocking filter 526 also passes a filtered first portion of the collimated broad spectrum light to the short pass filter 528. The infrared blocking filter 526 may be a 50% infrared blocking filter. The infrared blocking filter 526 may be Oriel® Instruments Model No. 59043 sold by Newport Corporation.

After the filtered first portion of the collimated broad spectrum light is passed by the infrared absorbing filter 526 to the short pass filter 528, the short pass filter 528 passes a second portion of the collimated broad spectrum light to the first dispersing lens 530. The short pass filter 528 may have a cut-off of 650 nm. If reflector 524 passes wavelengths greater than 650 nm, short pass filter 528 will block such wavelengths. If reflector 524 does not pass any wavelength greater than 650 nm, then short pass filter may not block any wavelength. The cut-off specified for short pass filter 528 can be less than, equal to or greater than highest wavelengths passed by short pass filter 528. Additionally, the cut-off specified for short pass filter 528 can be less than the highest wavelength passed by the reflector 524. The short pass filter 528 may be Andover Corporation Part No. 650-FL07-50. Different ranges can be passed to the first dispersing lens 530 depending on what light is reflected by the reflector 524 and passed by the short pass filter 528. For example, the second portion of the collimated broad spectrum light may have a given range of 400 nm to 630 nm. As another example, the range of wavelengths can be any variety of ranges, such as between about 595 nm and about 645 nm, between about 620 nm and about 640 nm, between about 615 nm and about 645 nm, or between about 610 nm and about 650 nm. Narrower band-pass filters can be used to reduce the range. The range of wavelengths can be centered on a given wavelength, such as 630 nm. A different center wavelength can be selected by changing components of the lighting system 500, such as the reflector 524 and the short pass filter 528. The first dispersing lens 530 can be arranged in a variety of configurations. In a first configuration, the first dispersing lens 530 may have a diameter of 3 in. Other diameters of the first dispersing lens 530 are possible. In that first configuration or another configuration, the first dispersing lens 530 may have an effective focal length of 200 mm. Other effective focal lengths of the first dispersing lens 530 are possible.

After the second portion of the collimated broad spectrum light is passed by the short pass filter 528 to the first dispersing lens 530, the first dispersing lens 530 passes the second portion of the broad spectrum light to the second dispersing lens 532. The second dispersing lens 532 can be arranged in a variety of configurations. In a first configuration, the second dispersing lens 532 may have a diameter of 3 in. Other diameters of the second dispersing lens 532 are possible. In that first configuration or another configuration, the second dispersing lens 532 may have an effective focal length of 200 mm. Other effective focal lengths of the second dispersing lens 532 are possible.

After the second portion of the collimated broad spectrum light is passed by the first dispersing lens 530 to the second dispersing lens 532, the second dispersing lens 532 disperses the second portion of the collimated broad spectrum light to the cell culture plate. The second dispersing lens 532 disperses the second portion of the collimated broad spectrum light to the cell culture plate through the first hole 544 for passing light and the second hole 560 for passing light. At least a portion of the first hole 544 for passing light may be above or below at least a portion of the second hole 560 for passing light.

The distance between the short pass filter 528 and the first dispersing lens 530, the gap between the first dispersing lens 530 and the second dispersing lens 532, and the distance between the short pass filter 528 and the cell culture plate may be selected to uniformly irradiate the cell culture plate. "Uniformly irradiate" and "uniform irradiation" refers to providing light dispersed by the second dispersing lens 532 to the entire area of the cell culture plate or to the entire bottom area of the cell culture plate.

The distance between the short pass filter 528 and the first dispersing lens 530 to uniformly irradiate the cell culture plate may be 13.6 cm. Other distances between the short pass filter 528 and the first dispersing lens 530 to uniformly irradiate the cell culture plate are possible. The distance can be a distance between portions of short pass filter 528 and the first dispersing lens 530 that are nearest each other. With respect to the orientation of lighting system 500 in FIG. 5, those portions can include a lower side of short pass filter 528 and an upper side of the first dispersing lens 530. Alternatively, the distance between the short pass filter 528 and the first dispersing lens 530 may be a distance between a vertical center point of the short pass filter 528 and a vertical center point of the first dispersing lens 530. Other examples of specifying the distance between the short pass filter 528 and the first dispersing lens 530 are possible.

The gap between the first dispersing lens 530 and the second dispersing lens 532 to uniformly irradiate the cell culture plate with the second portion of the broad spectrum light may be 3 mm. Other gaps between the first dispersing lens 530 and the second dispersing lens 532 are possible. For instance, the gap between the first dispersing lens 530 and the second dispersing lens 532 may be within the range of 2 mm to 4 mm, inclusive. The gap between the first dispersing lens 530 and the second dispersing lens 532 may be a distance between a closest point of the first dispersing lens 530 and a closest point of the second dispersing lens 532. Alternatively, the gap between the first dispersing lens 530 and the second dispersing lens 532 may be a distance between a vertical center point of the first dispersing lens 530 and a vertical center point of the second dispersing lens 532. Other examples of specifying the gap between the first dispersing lens 530 and the second dispersing lens 532 are possible.

The distance between the short pass filter 528 and the cell culture plate to uniformly irradiate the cell culture plate can be specified in various ways. In one respect, the distance can be specified as a distance from a highest point of short pass filter 528 to the external surface of the bottom area of the cell culture plate. In that regard, for a first case, the distance can be 95.5 cm. In another respect, the distance can be specified as a distance from the highest point of short pass filter 528 to the top area of the cell culture plate. In accordance with the first case referred to above, if the vertical wall (the distance between the top area of cell culture plate and the external surface of the bottom area of the cell culture plate) has a height of 1.42 cm, then the distance can be 94.08 cm. In another respect, the distance between the short pass filter 528 and the cell culture plate may be specified as a distance between a closest point of the short pass filter 528 and a closest point of the cell culture plate. In yet another respect, the distance between the short pass filter 528 and the cell culture plate may be specified as a distance between a vertical center point of the short pass filter 528 and a vertical center point of the cell culture plate. Other examples of specifying the distance between the short pass filter 528 and the cell culture plate are possible.

As noted above, the position of the first dispersing lens 530 and the second dispersing lens 532 in the direction perpendicular 536 to the wall 512 is adjustable by the first perpendicular adjustment slot 554, the first perpendicular adjustment fastener 555, the second perpendicular adjustment fastener 556, the second perpendicular adjustment slot 557, the third perpendicular adjustment fastener 558, and the fourth perpendicular adjustment fastener 559. With this arrangement, the position of the first dispersing lens 530 and the second dispersing lens 532 in the direction perpendicular 536 to the wall 512 may be adjusted to align a center of the first dispersing lens 530 with a center of the short pass filter 528. The position of the first dispersing lens 530 and the second dispersing lens 532 in a direction perpendicular 536 to the wall 512 may be adjusted by adjusting a location of the first perpendicular adjustment fastener 555 in the first perpendicular adjustment slot 554, adjusting a location of the second perpendicular adjustment fastener 556 in the first perpendicular adjustment slot 554, adjusting a location of the third perpendicular adjustment fastener 558 in the second perpendicular adjustment slot 557, and adjusting a location of the fourth perpendicular adjustment fastener 559 in the second perpendicular adjustment slot 557. The perpendicular adjustment fasteners (555, 556, 558, 559) may each be a bolt. The perpendicular adjustment fasteners (555, 556, 558, 559) may be other fasteners, such as screws. Adjusting the location of one of the perpendicular adjustment fasteners (555, 556, 558, 559) in one of the perpendicular adjustment slots (554, 557) may refer to translating the perpendicular adjustment fasteners (555, 556, 558, 559) within the perpendicular adjustment slots (554, 557).

As noted above, the gap between the first dispersing lens 530 and the second dispersing lens 532 is adjustable by the adjustment rod 533, the first adjustment spacer 534, and the second adjustment spacer 535. The gap between the first dispersing lens 530 and the second dispersing lens 532 may be adjusted by adjusting at least one position of the first adjustment spacer 534 and the second adjustment spacer 535 along the adjustment rod 533. The adjustment rod 533 may be threaded to engage with the first adjustment spacer 534 and the second adjustment spacer 535. The first adjustment spacer 534 may be a washer. Similarly, the second adjustment spacer 535 may be a washer.

As noted above, the position of the first dispersing lens 530 and the second dispersing lens 532 in the direction parallel 538 to the wall 512 is adjustable by the first parallel adjustment slot 550, the first parallel adjustment fastener 551, the second parallel adjustment slot 552, and the second parallel adjustment fastener 553. With this arrangement, the position of the first dispersing lens 530 and the second dispersing lens 532 in a direction parallel 538 to the wall 512 may be adjusted to align a center of the first dispersing lens 530 with a center of the short pass filter 528. The position of the first dispersing lens 530 and the second dispersing lens 532 in a direction parallel 538 to the wall 512 may be adjusted by adjusting a location of the first parallel adjustment fastener 551 in the first parallel adjustment slot 550 and adjusting a location of the second parallel adjustment fastener 553 in the second parallel adjustment slot 552. The first parallel adjustment fastener 551 and the second parallel adjustment fastener 553 may each be a screw. The first parallel adjustment fastener 551 and the second parallel adjustment fastener 553 may be other fasteners, such as a bolt with a corresponding nut. Adjusting the location of the first parallel adjustment fastener 551 in the first parallel adjustment slot 550 may refer to translating the first parallel adjustment fastener 551 within the first parallel adjustment slot 550. Similarly, adjusting the location of the second parallel adjustment fastener 553 in the second parallel adjustment slot 552 may refer to translating the second parallel adjustment fastener 553 within the second parallel adjustment slot 552.

As noted above, the lens slider 542 is removably attached to the shelf top 546. The lens slider may be removably attached to the shelf top by attaching the first perpendicular adjustment fastener 555 to the first lens slider attachment 561, attaching the second perpendicular adjustment fastener 556 to the second lens slider attachment 562, attaching the third perpendicular adjustment fastener 558 to the third lens slider attachment 563, and attaching the fourth perpendicular adjustment fastener 559 to the fourth lens slider attachment 564. The lens slider attachments (561, 562, 563, 564) may each be a hole or a slot with a corresponding nut (not shown). The lens slider attachments (561, 562, 563, 564) may be other attachments, such as a threaded hole. Other connections of the lens slider 542 to the shelf 540 are possible.

Although FIG. 7 shows the first lens slider attachment 561, the second lens slider attachment 562, the third lens slider attachment 563, and the fourth lens slider attachment 564 as being circular, a person skilled in the art will understand that 561, 562, 563, and 564 can be elongated slots to allow for additional adjustment of the first dispersing lens 530 and the second dispersing lens 532.

In an alternative embodiment, the reflector 524 is connected to the short pass filter 528. With this arrangement, the short pass filter 528 is connected to the infrared blocking filter 526.

In another embodiment, the light-port is connected to the infrared absorbing liquid filter 516. With this arrangement, the infrared absorbing liquid filter 516 is connected to the first lens, and the first lens is connected to the reflector 524.

In another embodiment, the first lens is outside of the light-port. With this arrangement, the light-port may be connected to the first lens, the first lens may be connected to the infrared absorbing liquid filter 516, and the infrared absorbing liquid filter 516 may be connected to the reflector 524. Alternatively, the light-port may be connected to the infrared absorbing liquid filter 516, the infrared absorbing liquid filter 516 may be connected to the first lens, and the first lens may be connected to the reflector 524. In accordance with these embodiments, the infrared blocking filter 526 or the short pass filter 528 should be downstream of the infrared absorbing liquid filter 516 or the reflector 524 to avoid the heat of the light cracking the infrared blocking filter 526 or the short pass filter 528.

In another embodiment, the lamp housing 502, the first lens, the infrared absorbing liquid filter 516, the reflector 524, the infrared blocking filter 526, the short pass filter 528, the first dispersing lens 530, and the second dispersing lens 532 are each positioned on a ledge (not shown) above a table (not shown). With this arrangement, the cell culture plate may then positioned on a temperature controlling device (not shown) located on the table. The temperature controlling device can be arranged in various configurations. For instance, the temperature controlling device may be a heating device or a cooling device. The temperature control device may maintain the cell culture plate, as well as the contents of the cell culture plate, at a regulated temperature.

In yet another embodiment, the reflector 524 is inverted. With this arrangement, the reflector 524 reflects the first portion of the collimated broad spectrum light upward. As such, the infrared blocking filter 526, the short pass filter 528, the first dispersing lens 530, the second dispersing lens 532, and the cell culture plate are each located above the reflector 524. In accordance with this embodiment, uniform irradiation of the cell culture plate comprises providing light dispersed by the second dispersing lens 532 to the entire bottom area of the cell culture plate.

FIGS. 8A-C and 9 illustrate another embodiment of a lighting system generally designated 800 and components thereof. The lighting system 800 includes a lamp housing 802, a first lens (not shown), an infrared absorbing liquid filter 816, an inlet cooling tube 818, and outlet cooling tube 820, a supporting member 821, a pump 822, a cooling system 823, a reflector 824, an infrared blocking filter 826, a short pass filter 828, a first plano convex lens 830, a first plano convex lens holder 870, a second plano convex lens 832, a second plano convex lens holder 872, an adjustment rod 841, a first adjustment spacer 842, a second adjustment spacer 843, a base wall 848, a shelf 850, a lens slider 852, and cell culture plate (not shown). The lamp housing 802 includes a lamp (not shown), a mirror (not shown), a light-port (not shown), a top 808, a bottom 810, and a wall 812. The first plano convex lens 830 includes a first convex side 836 and a first plane side (not shown). The second plano convex lens 832 includes a second convex side 840 and a second plane side (not shown). The shelf 850 includes a shelf top 854, a shelf riser 856, a first parallel adjustment slot 858, a first parallel adjustment fastener 859, a second parallel adjustment slot 860, a second parallel adjustment fastener 861, a second hole 868 for passing light, a race (not shown), a first lens slider attachment (not shown), a second lens slider attachment (not shown), a third lens slider attachment (not shown), and a fourth lens slider attachment (not shown). The lens slider 852 includes a first perpendicular adjustment slot 862, a first perpendicular adjustment fastener 863, a second perpendicular adjustment fastener 864, a second perpendicular adjustment slot 865, a third perpendicular adjustment fastener 866, a fourth perpendicular adjustment fastener 867, and a first hole (not shown) for passing light.

In the lighting system 800, the lamp is within the lamp housing 802 like the lamps in the lighting systems illustrated in FIGS. 1-4. The light-port is within the lamp housing 802 like the light-ports in the lighting systems illustrated in FIGS. 1-4. The first lens is within the light-port like the first lenses in the lighting systems illustrated in FIGS. 1-4. The first lens, the infrared absorbing liquid filter 816, the reflector 824, the infrared blocking filter 826, and the short pass filter 828 are each located at positions between the top 808 and the bottom 810. The bottom 810 can be metal.

Additionally, in the lighting system 800, the infrared absorbing liquid filter 816 is connected to the light-port like the infrared absorbing filters are connected to the light-ports in the lighting systems illustrated in FIGS. 1-4. The infrared absorbing liquid filter 816 is connected to the inlet cooling tube 818. The inlet cooling tube 818 is supported by the supporting member 821. The inlet cooling tube 818 is connected to the pump 822. The pump 822 is connected to the cooling system 823. The connection can be in-line. The infrared absorbing liquid filter 816 is connected to the outlet cooling tube 820. The outlet cooling tube 820 is supported by the supporting member 821. The outlet cooling tube 820 is connected to the pump 822.

Figure 8A:
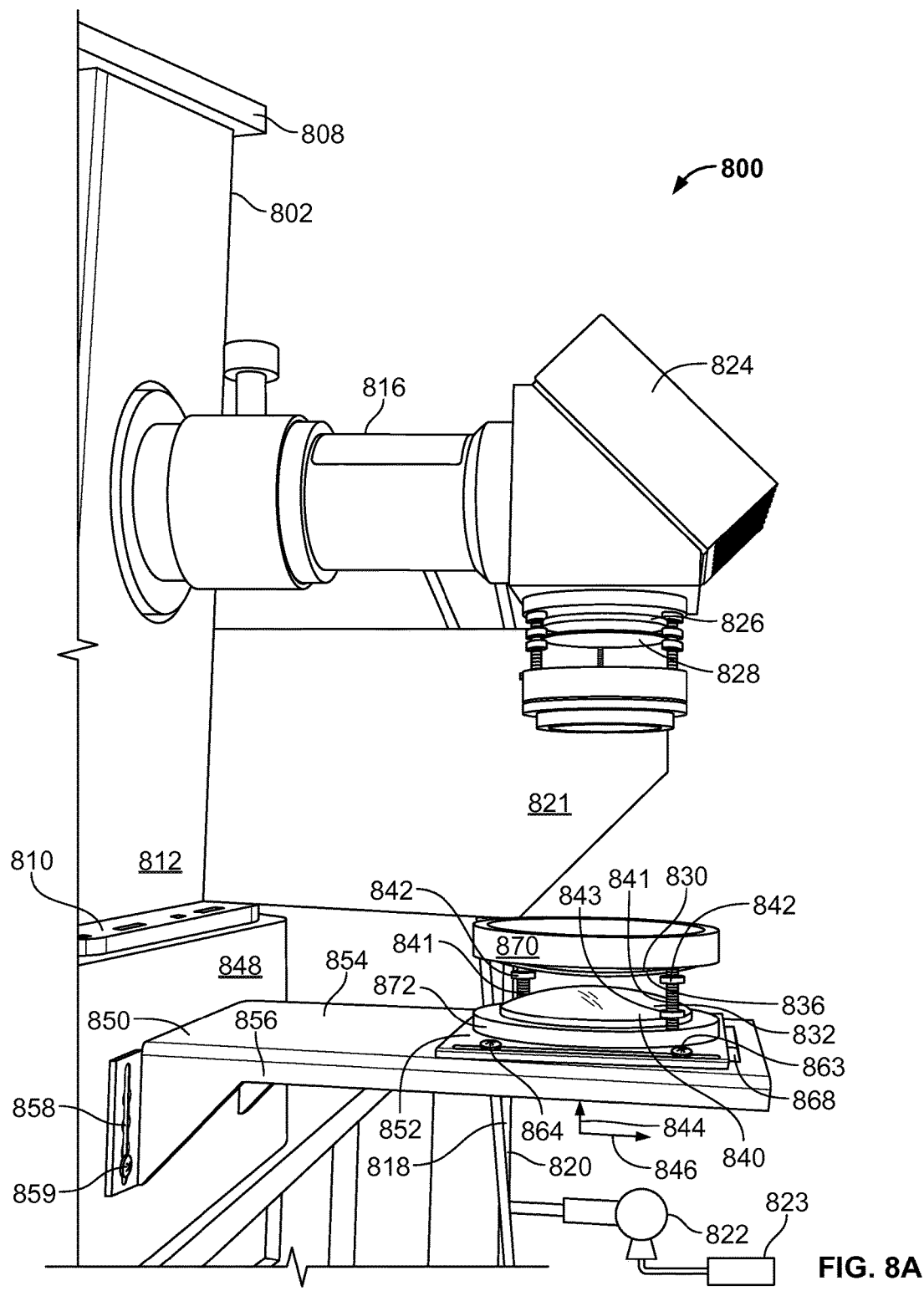
FIG. 8A is a side elevational view of another embodiment lighting system.
Figure 8B:
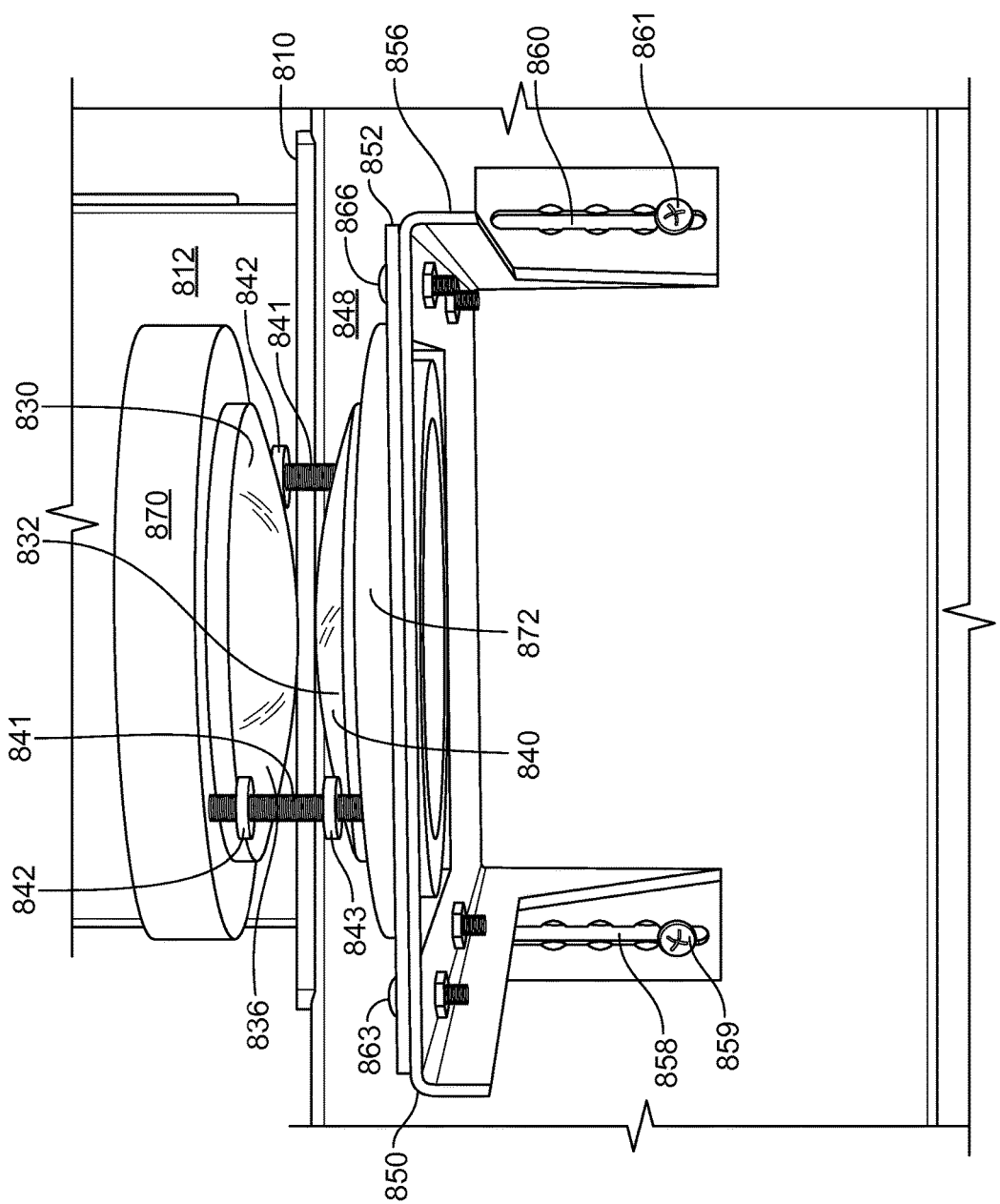
FIG. 8B is a front elevational view of the shelf and related components of the lighting system illustrated in FIG. 8A.
Figure 8C:
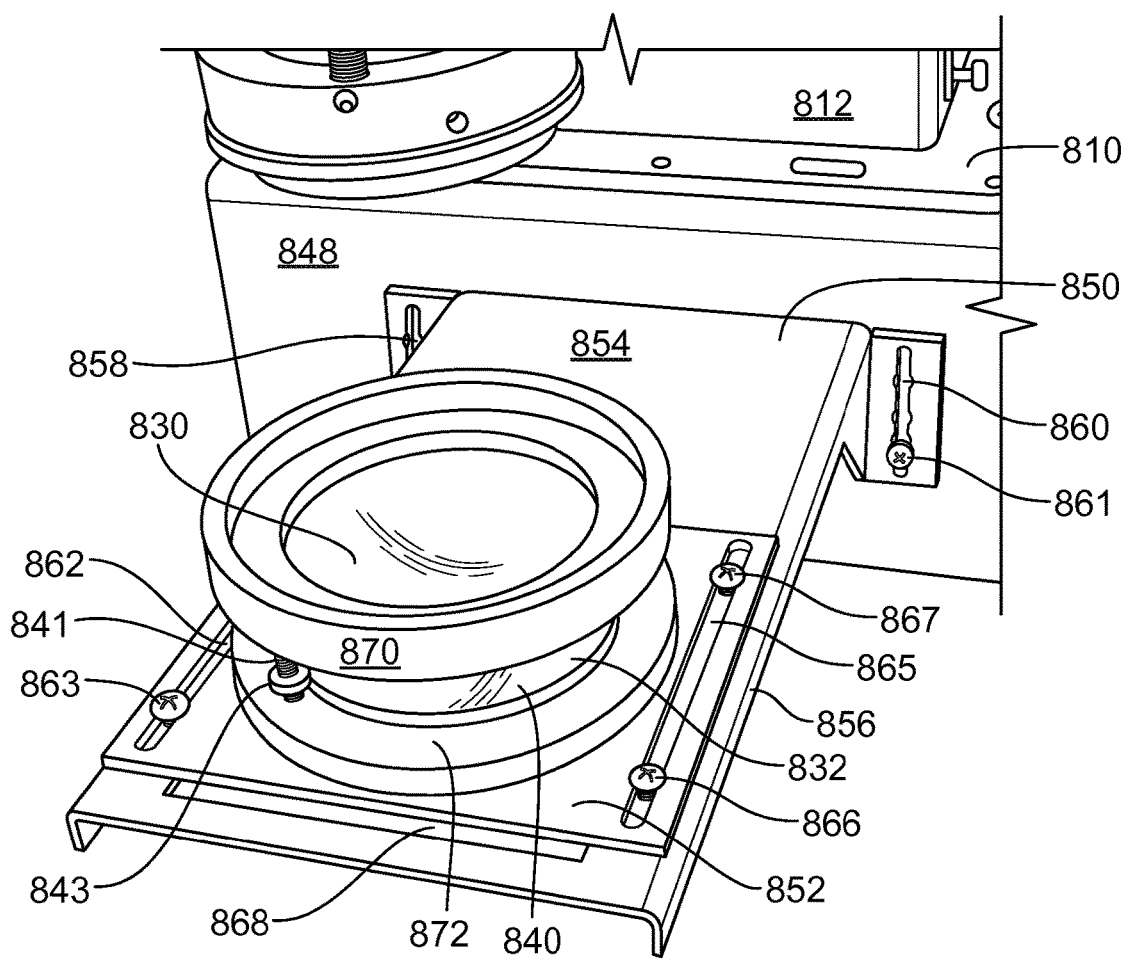
FIG. 8C is a perspective view of the lens slider and related components of the lighting system illustrated in FIG. 8A.
Figure 9:
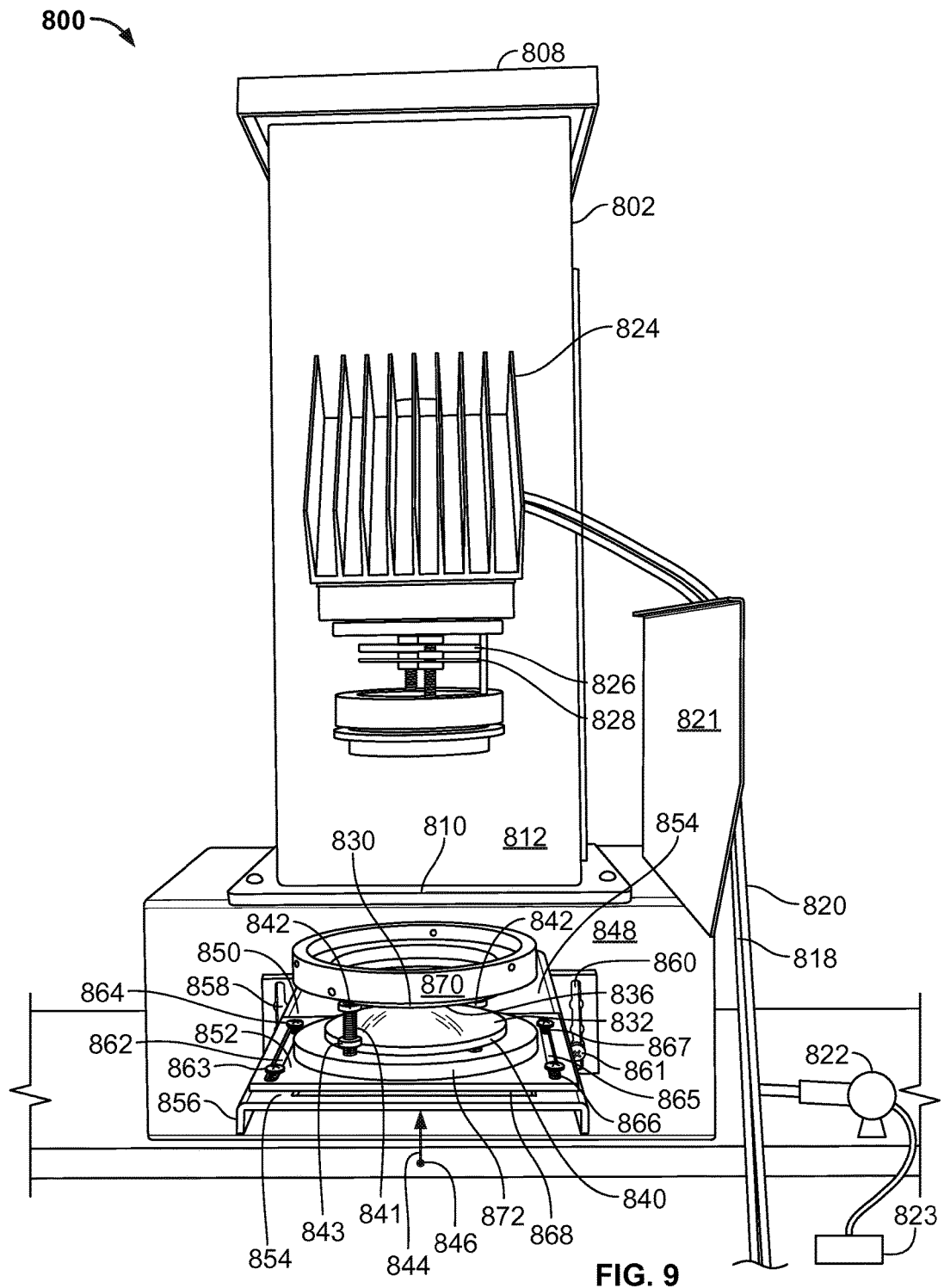
FIG. 9 is a front elevational view of the lighting system illustrated in FIG. 8A.

Additionally, in the lighting system 800, the reflector 824 is connected to the infrared absorbing liquid filter 816. The infrared blocking filter 826 is connected to the reflector 824. The short pass filter 828 is connected to the infrared blocking filter 826. The first plano convex lens 830 is located a distance from the infrared blocking filter 826 like the second lenses are located a distance from the optical filters in the lighting systems illustrated in FIGS. 1-4. The first plano convex lens 830 is supported by the first plano convex lens holder 870. The first plano convex lens 830 is adjacent to the second plano convex lens 832 with a gap between the first convex side 836 and the second convex side 840. The gap between the first convex side 836 and the second convex side 840 is adjustable by the adjustment rod 841, the first adjustment spacer 842, and the second adjustment spacer 843. Two adjustment rods 841 each with the first adjustment spacer 842 and the second adjustment spacer 843 are shown in FIG. 8A and can be sufficient to adjust the gap between the first convex side 836 and the second convex side 840. In some embodiments, three or more adjustment rods 841 each with the first adjustment spacer 842 and the second adjustment spacer 843 equally spaced around the first plano convex lens 830 and the second plano convex lens 832 are possible. The second plano convex lens 832 is supported by the second plano convex lens holder 872. The second plano convex lens holder 872 is removably attached to the lens slider 852. More specifically, the second plano convex lens holder 872 comprises a flange (not shown) that rests on the lens slider 852. A portion of the second dispersing lens holder 872 can be positioned within the first hole for passing light or within the first hole and the second hole 868 for passing light. Alternatively, a portion of the second plano convex lens holder 872 can extend beyond the first hole for passing light and the second hole 868 for passing light. The lens slider 852 is removably attached to the shelf top 854. The shelf 850 is connected to the base wall 848. The shelf riser 856 is located in a direction parallel 844 to the wall 812. The shelf top 854 is located in a direction perpendicular 846 to the wall 812. A position of the first plano convex lens 830 and the second plano convex lens 832 is adjustable in the direction parallel 844 to the wall 812. A position of the first plano convex lens 830 and the second plano convex lens 832 is adjustable in the direction perpendicular 846 to the wall 812.

Components in the lighting system 800 can be arranged like the components in the lighting system 500 illustrated in FIGS. 5-7. For example, the lamp housing 802 can be arranged like the lamp housing 502, the lamp can be arranged like the lamp, the light-port can be arranged like the light-port, the first lens can be arranged like the first lens of the lighting system 500, the mirror can be arranged like the mirror of the lighting system 500, the infrared absorbing liquid filter 816 can be arranged like the infrared absorbing liquid filter 516, the inlet cooling tube 818 can be arranged like the inlet cooling tube 518, the outlet cooling tube 820 can be arranged like the outlet cooling tube 520, the pump 822 can be arranged like the pump 522, the cooling system 823 can be arranged like the cooling system 523, the reflector 824 can be arranged like the reflector 524, the infrared blocking filter 826 can be arranged like the infrared blocking filter 526, the short pass filter 828 can be arranged like the short pass filter 528, the shelf 850 can be arranged like the shelf 540, the shelf top 854 can be arranged like the shelf top 546, the shelf riser 856 can be arranged like the shelf riser 548, the first parallel adjustment slot 858 can be arranged like the first parallel adjustment slot 550, the first parallel adjustment fastener 859 can be arranged like the first parallel adjustment fastener 551, the second parallel adjustment slot 860 can be arranged like the second parallel adjustment slot 552, the second parallel adjustment fastener 861 can be arranged like the second parallel adjustment fastener 553, the second hole 868 for passing light can be arranged like the second hole 560 for passing light, the first lens slider attachment can be arranged like the first lens slider attachment 561, the second lens slider attachment can be arranged like the second lens slider attachment 562, the third lens slider attachment can be arranged like the third lens slider attachment 563, the fourth lens slider attachment can be arranged like the fourth lens slider attachment 564, the race can be arranged like the race 565, the lens slider 852 can be arranged like the lens slider 542, the first perpendicular adjustment slot 862 can be arranged like the first perpendicular adjustment slot 554, the first perpendicular adjustment fastener 863 can be arranged like the first perpendicular adjustment fastener 555, the second perpendicular adjustment fastener 864 can be arranged like the second perpendicular adjustment fastener 556, the second perpendicular adjustment slot 865 can be arranged like the second perpendicular adjustment slot 557, the third perpendicular adjustment fastener 866 can be arranged like the third perpendicular adjustment fastener 558, the fourth perpendicular adjustment fastener 867 can be arranged like the fourth perpendicular adjustment fastener 559, and the first hole for passing light can be arranged like the first hole 544 for passing light. Additionally, the cell culture plate can be arranged like the cell culture plate 120 in the lighting system 100 illustrated in FIG. 1.

In operation, the cell culture plate, as well as the contents of the cell culture plate, is irradiated with light from the lamp. First, broad spectrum light from the lamp exits the lamp by passing through the light-port. The broad spectrum light may be reflected by the mirror to the light-port.

After the broad spectrum light exits the lamp housing 802 by passing through the light-port, the broad spectrum light is collimated by the first lens.

After the broad spectrum light is collimated by the first lens, the collimated broad spectrum light reaches the infrared absorbing liquid filter 816. The infrared absorbing liquid filter 816 absorbs infrared light of the collimated broad spectrum light. The infrared absorbing liquid filter 816 may absorb between 90% and 100%, inclusive, of the infrared light of the broad spectrum light. Other infrared absorbing ranges of the infrared absorbing liquid filter 816 are possible. The temperature of the infrared absorbing liquid filter 816 may be controlled by pumping a cooling fluid to a jacket (not shown) of the infrared absorbing liquid filter 816 at a flow rate through the inlet cooling tube 818 and the outlet cooling tube 820 using the pump 822. The cooling fluid may be ice-cold water. The cooling fluid may be cooled by the cooling system 823. The flow rate may be 6 mL/min. The infrared absorbing liquid filter 816 also passes a first portion of the collimated broad spectrum light to the reflector 824.

After the first portion of the collimated broad spectrum light is passed by the infrared absorbing liquid filter 816 to the reflector 824, the reflector 824 reflects the first portion of the collimated broad spectrum light. The first portion of the collimated broad spectrum light then propagates to the infrared blocking filter 826. Alternatively, the reflector 824 may reflect only a portion of the first portion of the collimated broad spectrum light, and the portion of the first portion of the collimated broad spectrum light then propagates to the infrared blocking filter 826. The reflector 824 reflects light with the same given range of wavelengths as the reflector 524.

After the first portion of the broad spectrum light propagates to the infrared blocking filter 826, the infrared blocking filter 826 absorbs residual infrared light of the first portion of the collimated broad spectrum light. The infrared blocking filter 826 also passes a filtered first portion of the broad spectrum light to the short pass filter 828.

After the filtered first portion of the collimated broad spectrum light is passed by the infrared blocking filter 826 to the short pass filter 828, the short pass filter 828 passes a second portion of the broad spectrum light to the first plano convex lens 830. The short pass filter 828 passes light with the same given range of wavelengths as the short pass filter 528. The first plano convex lens 830 can be arranged in a variety of configurations. In a first configuration, the first plano convex lens 830 may have a diameter of 3 in. Other diameters of the first plano convex lens 830 are possible. In that first configuration or another configuration, the first plano convex lens 830 may have an effective focal length of 200 mm. Other effective focal lengths of the first plano convex lens 830 are possible. The first plano convex lens 830 may be Newport Corporation Part No. KPX229.

After the second portion of the collimated broad spectrum light is passed by the short pass filter 828 to the first plano convex lens 830, the first plano convex lens 830 passes the second portion of the collimated broad spectrum light to the second plano convex lens 832. The second plano convex lens 832 can be arranged in a variety of configurations. In a first configuration, the second plano convex lens 832 may have a diameter of 3 in. Other diameters of the second plano convex lens 832 are possible. In that first configuration or another configuration, the second plano convex lens 832 may have an effective focal length of 200 mm. Other effective focal lengths of the second plano convex lens 832 are possible. The second plano convex lens 832 may be Newport Corporation Part No. KPX299. The first plano convex lens holder 870 and the second plano convex lens holder 872 may be individual components or a single unit, such as Newport Corporation Part No. 6216.

After the second portion of the collimated broad spectrum light is passed by the first plano convex lens 830 to the second plano convex lens 832, the second plano convex lens 832 disperses the second portion of the collimated broad spectrum light to the cell culture plate. The second plano convex lens 832 disperses the second portion of the collimated broad spectrum light to the cell culture plate through the first hole for passing light and the second hole 868 for passing light. At least a portion of the first hole for passing light may be above or below at least a portion of the second hole 868 for passing light.

The distance between the short pass filter 828 and the first plano convex lens 830, the gap between the first convex side 836 and the second convex side 840, and the distance between the second plano convex lens 832 and the cell culture plate may be selected to uniformly irradiate the cell culture plate. "Uniformly irradiate" and "uniform irradiation" refers to providing light dispersed by the second plano convex lens 832 to the entire area of the cell culture plate or to the entire bottom area of the cell culture plate.

The distance between the short pass filter 828 and the first plano convex lens 830 to uniformly irradiate the cell culture plate may be 13.6 cm. Other distances between the short pass filter 828 and the first plano convex lens 830 to uniformly irradiate the cell culture plate are possible. The distance can be a distance between portions of short pass filter 828 and the first plano convex lens 830 that are nearest each other. With respect to the orientation of lighting system 800 in FIGS. 8A-C and 9, those portions can include a lower side of short pass filter 828 and an upper side of the first plano convex lens 830. Alternatively, the distance between the short pass filter 828 and the first plano convex lens 830 may be a distance between a vertical center point of the short pass filter 828 and a vertical center point of the first plano convex lens 830. Other examples of specifying the distance between the short pass filter 828 and the first plano convex lens 830 are possible.

The gap between the first convex side 836 and the second convex side 840 to uniformly irradiate the cell culture plate with the second portion of the broad spectrum light may be 3 mm. Other gaps between the first convex side 836 and the second convex side 840 are possible. For instance, the gap between the first convex side 836 and the second convex side 840 may be within the range of 2 mm to 4 mm, inclusive. The gap between the first convex side 836 and the second convex side 840 may be a distance between a closest point of the first convex side 836 and a closest point of the second convex side 840. Alternatively, the gap between the first convex side 836 and the second convex side 840 may be a distance between a vertical center point of the first convex side 836 and a vertical center point of the second convex side 840. Other examples of specifying the gap between the first convex side 836 and the second convex side 840 are possible.

The distance between the short pass filter 828 and the cell culture plate to uniformly irradiate the cell culture plate can be specified in various ways. In one respect, the distance can be specified as a distance from a highest point of short pass filter 828 to the external surface of the bottom area of the cell culture plate. In that regard, for a first case, the distance can be 95.5 cm. In another respect, the distance can be specified as a distance from the highest point of short pass filter 828 to the top area of the cell culture plate. In accordance with the first case referred to above, if the vertical wall (the distance between the top area of cell culture plate and the external surface of the bottom area of the cell culture plate) has a height of 1.42 cm, then the distance can be 94.08 cm. In another respect, the distance between the short pass filter 828 and the cell culture plate may be specified as a distance between a closest point of the short pass filter 828 and a closest point of the cell culture plate. In yet another respect, the distance between the short pass filter 828 and the cell culture plate may be specified as a distance between a vertical center point of the short pass filter 828 and a vertical center point of the cell culture plate. Other examples of specifying the distance between the short pass filter 828 and the cell culture plate are possible.

As noted above, the position of the first plano convex lens 830 and the second plano convex lens 832 in the direction parallel 844 to the wall 812 is adjustable by the first parallel adjustment slot 858, the first parallel adjustment fastener 859, the second parallel adjustment slot 860, and the second parallel adjustment fastener 861. With this arrangement, the position of the first plano convex lens 830 and the second plano convex lens 832 in the direction parallel 844 to the wall 812 may be adjusted to align a center of the first plano convex lens 830 with a center of the short pass filter 828. The position of the first plano convex lens 830 and the second plano convex lens 832 in the direction parallel 844 to the wall 812 may be adjusted by adjusting a location of the first parallel adjustment fastener 859 in the first parallel adjustment slot 858 and adjusting a location of the second parallel adjustment fastener 861 in the second parallel adjustment slot 860. Adjusting the location of the first parallel adjustment fastener 859 in the first parallel adjustment slot 858 may refer to translating the first parallel adjustment fastener 859 within the first parallel adjustment slot 858. Similarly, adjusting the location of the second parallel adjustment fastener 861 in the second parallel adjustment slot 860 may refer to translating the second parallel adjustment fastener 861 within the second parallel adjustment slot 860.

As noted above, the gap between the first convex side 836 and the second convex side 840 is adjustable by the adjustment rod 841, the first adjustment spacer 842, and the second adjustment spacer 843. The gap between the first convex side 836 and the second convex side 840 may be adjusted by adjusting at least one position of the first adjustment spacer 842 and the second adjustment spacer 843 along the adjustment rod 841. The adjustment rod 841 may be threaded to engage with the first adjustment spacer 842 and the second adjustment spacer 843.

As noted above, the position of the first plano convex lens 830 and the second plano convex lens 832 in the direction perpendicular 846 to the wall 812 is adjustable by the first perpendicular adjustment slot 862, the first perpendicular adjustment fastener 863, the second perpendicular adjustment fastener 864, the second perpendicular adjustment slot 865, the third perpendicular adjustment fastener 866, and the fourth perpendicular adjustment fastener 867. With this arrangement, the position of the first plano convex lens 830 and the second plano convex lens 832 in the direction perpendicular 846 to the wall 812 may be adjusted to align the center of the first plano convex lens 830 with the center of the short pass filter 828. The position of the first plano convex lens 830 and the second plano convex lens 832 in a direction perpendicular 846 to the wall 812 may be adjusted by adjusting a location of the first perpendicular adjustment fastener 863 in the first perpendicular adjustment slot 862, adjusting a location of the second perpendicular adjustment fastener 864 in the first perpendicular adjustment slot 862, adjusting a location of the third perpendicular adjustment fastener 866 in the second perpendicular adjustment slot 865, and adjusting a location of the fourth perpendicular adjustment fastener 867 in the second perpendicular adjustment slot 865. Adjusting the location of one of the perpendicular adjustment fasteners (863, 864, 866, 867) in one of the perpendicular adjustment slots (862, 865) may refer to translating the perpendicular adjustment fasteners (863, 864, 866, 867) within the perpendicular adjustment slots (862, 865).

In an alternative embodiment, the reflector 824 is connected to the short pass filter 828. With this arrangement, the short pass filter 828 is connected to the infrared blocking filter 826.

In another embodiment, the light-port is connected to the infrared absorbing liquid filter 816. With this arrangement, the infrared absorbing liquid filter 816 is connected to the first lens, and the first lens is connected to the reflector 824.

In another embodiment, the first lens is outside of the light-port. With this arrangement, the light-port may be connected to the first lens, the first lens may be connected to the infrared absorbing liquid filter 816, and the infrared absorbing liquid filter 816 may be connected to the reflector 824. Alternatively, the light-port may be connected to the infrared absorbing liquid filter 816, the infrared absorbing liquid filter 816 may be connected to the first lens, and the first lens may be connected to the reflector 824. In accordance with these embodiments, the infrared blocking filter 826 or the short pass filter 828 should be downstream of the infrared absorbing liquid filter 816 or the reflector 824 to avoid the heat of the light cracking the infrared blocking filter 826 or the short pass filter 828.

In another embodiment, the lamp housing 802, the first lens, the infrared absorbing liquid filter 816, the reflector 824, the infrared blocking filter 826, the short pass filter 828, the first plano convex lens 830, and the second plano convex lens 832 are each positioned on a ledge (not shown) above a table (not shown). With this arrangement, the cell culture plate is then positioned on a temperature controlling device (not shown) located on the table. The temperature controlling device can be arranged in various configurations. For instance, the temperature controlling device may be a heating device or a cooling device. The temperature controlling device may maintain the cell culture plate, as well as the contents of the cell culture plate, at a regulated temperature.

In yet another embodiment, the reflector 824 is inverted. With this arrangement, the reflector 824 reflects the first portion of the collimated broad spectrum light upward. As such, the infrared blocking filter 826, the short pass filter 828, the first plano convex lens 830, the second plano convex lens 832, and the cell culture plate are each located above the reflector 824. In accordance with this embodiment, uniform irradiation of the cell culture plate comprises providing light dispersed by the second plano convex lens 832 to the entire bottom area of the cell culture plate.

For any of the embodiments of the lighting systems described herein, a light meter can measure light, detectable by a probe, between the lamp and the cell culture plate. The light meter may be a hand held power meter, such as Newport Corporation Part No. 1916-R. The probe may be a meter probe or sensor, such as Newport Corporation Part No. 818P-001-12.

2. Example Operation

The lighting system 100 may be used to irradiate contents of a cell culture plate 120. This method is applicable to any of the example lighting systems discussed above. The cell culture plate may comprise a photosensitizer.

Figure 10:
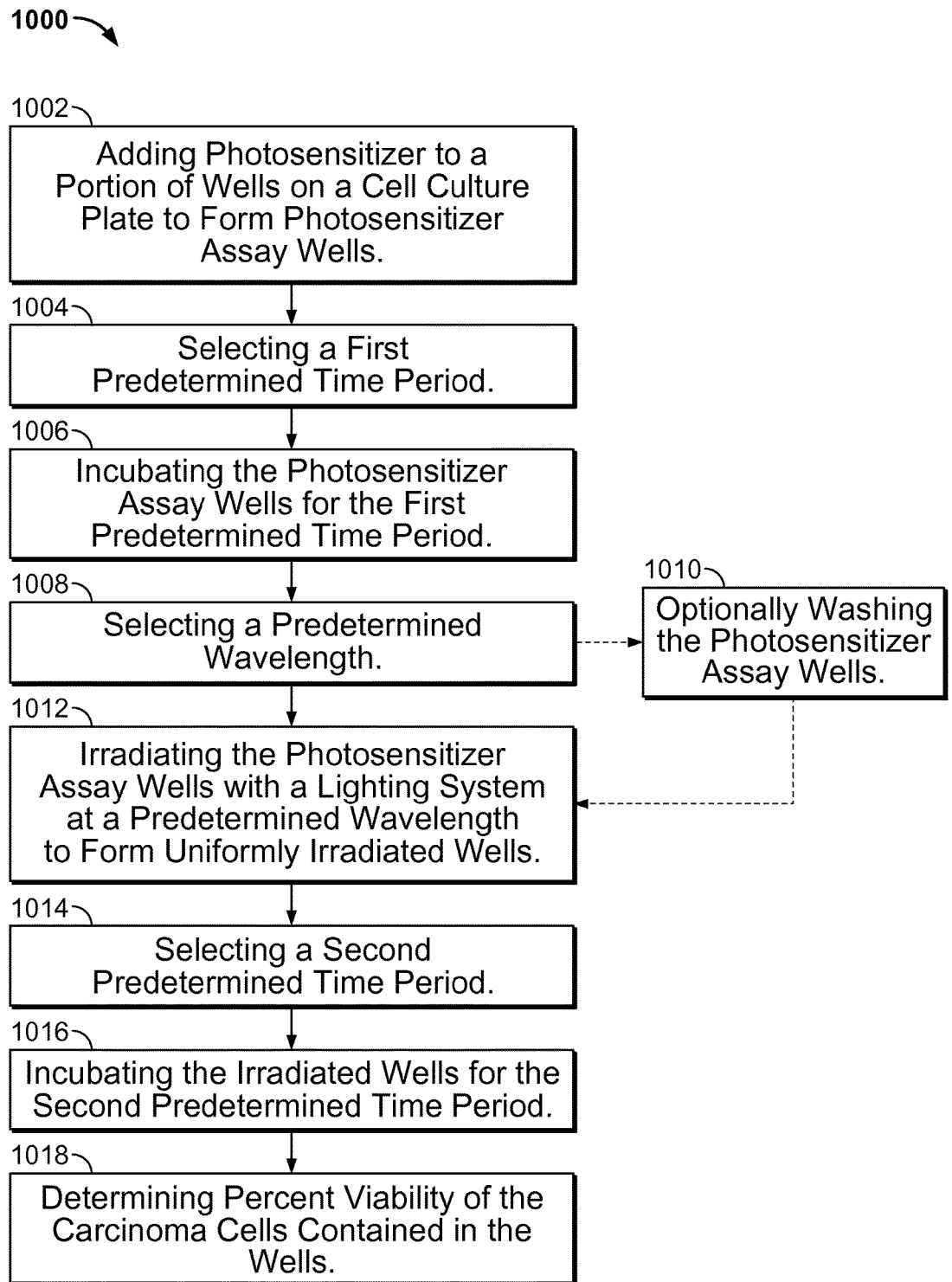
FIG. 10 is a flow chart of a method of using a lighting system constructed in accordance with principles disclosed herein to irradiate contents of a cell culture plate.

A method 1000 for studying a photosensitizer is provided as shown in FIG. 10. The method 1000 comprises adding the photosensitizer to a portion of wells on a cell culture plate to form photosensitizer assay wells (1002), the wells comprising carcinoma cells, selecting a first predetermined time period (1004), and incubating the photosensitizer assay wells for the first predetermined time period (1006). The carcinoma cells may be, for example, A549 human lung carcinoma cells. The method may also be used with any type of cell line, such as carcinoma, tumor, and normal cell lines. The cell culture plate may be an opaque black plate.

The method 1000 further comprises selecting a predetermined wavelength (1008) and optionally washing the photosensitizer assay wells (1010). The method 1000 also comprises irradiating the photosensitizer assay wells with the lighting system at the predetermined wavelength to form irradiated wells to form uniformly irradiated wells (1012). For example, the photosensitizer assay wells may be irradiated at between about 400 nm and about 650 nm. In other embodiments, the photosensitizer assay wells may be irradiated at different wavelengths, for example between about 595 nm and about 645 nm, between about 620 nm and about 640 nm, between about 615 nm and about 645 nm, or between about 610 nm and about 650 nm. Depending on the type of photosensitizer used, different wavelengths may be used. The irradiating step may be standardized such that the step is repeated in the same way each time. The lighting system 100 discussed in detail above provides for this standardization.

The method 1000 further comprises selecting a second predetermined time period (1014), incubating the irradiated wells for the second predetermined time period (1016), and determining percent viability of the carcinoma cells contained in the wells (1018).

In some embodiments, the step of washing the photosensitizer assay wells (1010) is mandatory. The remaining portion of the wells may be control wells. A portion of the wells may contain a reference drug used for comparison.

The photosensitizer is a porphyrin-based anti-neoplastic agent and the porphyrin-based anti-neoplastic agent may be porfimer sodium.

Examples

1. Overview

Cell passaging of A549 cells is performed using fixed seeding densities to reduce assay variation resulting from cell culture conditions. For each assay, cells are seeded into sterile, black, tissue-cultured treated 96-well plates at 10,000 cells per well in a 0.1 mL volume and incubated at 37° C. in an atmosphere of 5% $CO_2$ overnight. Working in very low light conditions, Photofrin® is reconstituted in normal saline to 2.5 mg/mL and diluted further in culture medium at twice the desired final assay concentration, typically 140 µg/mL. A series of two-fold dilutions were then prepared from the 140 µg/mL solution and the diluted drug was added to the cells at 1:1 (v/v) according to the diagram shown in FIG. 11.

The plate is covered with a black lid and placed in the incubator for four hours to allow absorption of the drug by the cells. The plate is then removed from the incubator, the drug is aspirated, the wells are washed with Dulbecco's phosphate buffered saline (DPBS) and fresh, pre-warmed medium is added to the wells. The columns of wells not to be irradiated are covered with foil strips, the black lid is exchanged for a clear lid, and the plate is then moved to the irradiation template beneath the light beam and irradiated for ten minutes, for a total of 3.3 joules. The plate is returned to the incubator and assessed for viability using XTT after 24 hours. The wells covered with foil strips are important controls for the activity of Photofrin® in the absence of irradiation and the effect of light on the cells in the absence of drug.

The optical absorbance of the wells in column 1 (high drug concentration, no cells) is evaluated for absorption at 450 nm to ensure that the drug is not interfering with the XTT assay. The percent viability of each of the wells in columns 2-9 and 11 is calculated relative to the mean value of column 10 (cell control, no drug, no light). For each dose response obtained, a four parameter logistic (4PL) nonlinear regression analysis is performed of the percent viability versus the log-Photofrin® concentration. The point of inflection of the regression curve (C value) is defined as the $EC_{50}$ and used in the calculation of relative potency. Curve fitting and calculation of the $EC_{50}$ is performed with Softmax v5.4.2 (Molecular Devices, Inc.) or Prism v.5.04 (GraphPad, Software Inc.) software. The mean percent viability of columns 9 and 11 is also calculated.

Figures 11, 12:
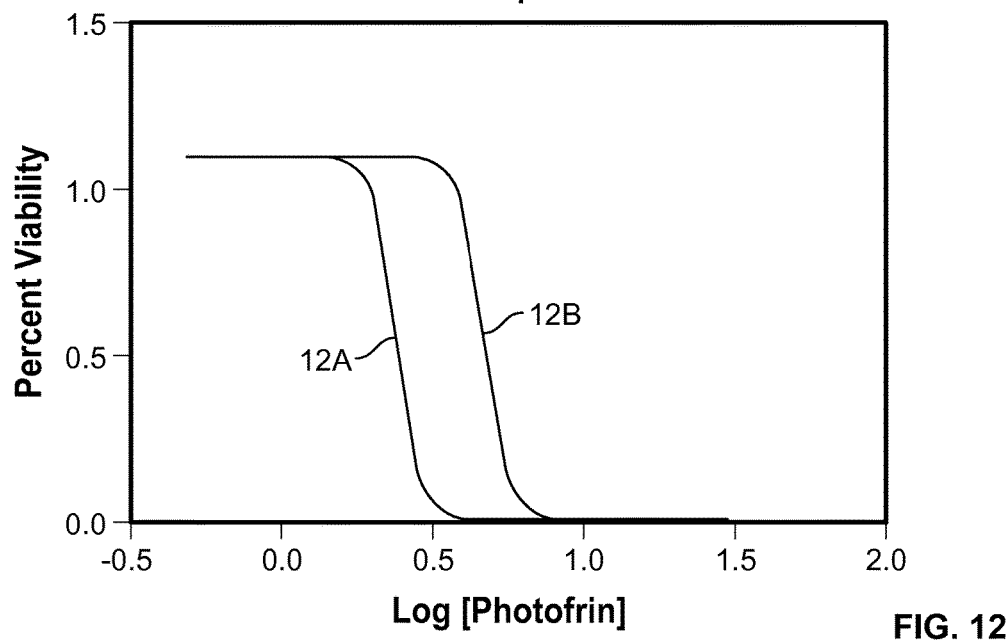
FIG. 11 is a diagram of plate layout for Photofrin® potency assay.
FIG. 12 is a graphical representation of Photofrin® dose-response of A549 cells.

A typical assay result is shown in FIG. 12. The sigmoidal curve on the left is the dose-response curve of a standard preparation of Photofrin®, while the curve on the right is the dose-response curve of a Photofrin® preparation containing half of the nominal activity. The ration of the standard to test sample $EC_{50}$ is 0.5.

The invention described herein can be modified for the irradiation of cells at different wavelengths by selection of the appropriate filters, including infrared or ultraviolet wavelengths. Depending on the cell type, drug, and filter efficiency, the drug absorption and irradiation times can be varied to obtain the desired results.

2. Detailed Methods

Method for Thawing A549 Cells

1. Materials and Reagents
    1.1. A549 Human Lung Carcinoma (ATCC—Cat. No.: CCL-185)

1.2. 25 cm² Flasks (Corning—Cat. No.: 431463, or equivalent)
1.3. 75 cm² Flasks (Corning—Cat. No.: 431464, or equivalent)
1.4. 50 mL tubes (Fisher Scientific—Cat. No. 17-512F, or equivalent)
1.5. Hemacytometer
1.6. RPMI-1640 (+) phenol red (Lonza—Cat. No.: 12-167F, or equivalent)
1.7. HI-FBS (Gibco—Life Technologies—Cat No.: 10082-147, or equivalent)
1.8. 200 mM L-Glutamine (Lonza—Cat. No.: 17-605E, or equivalent)
1.9. 0.25% Trypsin-EDTA (Gibco—Cat. No.: 25200-056, or equivalent)
2. Instruments
    2.1. Forma Scientific centrifuge with swinging bucket rotor (Model 5682, or equivalent)
    2.2. Water bath set at 37° C.
    2.3. Humidified incubator set at 37° C. with 5% CO2
3. Prepared Reagents
    3.1. RPMI-1640 Complete Media
        3.1.1. 500 mL bottle of RPMI-1640 basal media containing phenol red
        3.1.2. Add 50 mL HI-FBS
        3.1.3. Add 5.5 mL of 200 mM L-Glutamine
4. Procedure
    4.1. Remove one vial of A549 lung carcinoma cells from liquid nitrogen storage and after ensuring that the vial is tightly closed, rapidly thaw vial by holding all but the top of the vial submerged in a 37° C. water bath until the vial contents begins to thaw but while ice still remains.
    4.2. Liberally spray the vial with 70% ethanol, wipe with tissue, and place into a laminar flow hood.
    4.3. Transfer the contents of the vial to a 50 mL conical tube containing 9 mL RPMI-1640 complete medium containing phenol red (Step 3.1) (hereafter referred to as complete medium in this method).
    4.4. Centrifuge the tube in a swing bucket rotor set at 1200 RPM (220 RCF) for five minutes at room temperature.
    4.5. Discard supernatant and gently flick the tube to resuspend the cells in the residual volume left in the tube.
    4.6. Add 5 mL complete medium, transfer the cell solution to a 25 cm² flask, and then place the flask into a 37° C. incubator with 5% CO2.
    4.7. Monitor the flask daily and when the cells reach approximately 80% confluence, remove the media, and wash the cells by adding 2 mL DPBS to the flask. Ensure that all cells are rinsed and discard the DPBS.
    4.8. Add 1 mL 0.25% trypsin-EDTA to prewash the cells, tip flask to coat all cells, and discard the trypsin.
    4.9. Add another 1 mL trypsin, tip to coat all cells, and then place into a 37° C. incubator for 4 minutes or until cells detach.
    4.10. Stop the trypsin reaction by adding 4 mL complete media to the flask and then collect all cells and transfer to a 50 mL conical tube.
    4.11. Count the cell solution using a hemacytometer and seed the cells into the appropriate number of 75 cm² flasks as needed using the following seeding densities:

| Day Cell Needed | Seeding Density |
| --- | --- |
| For Day 3 | Add 0.4 × 10E+06 cells/75 cm2 flask |
| For Day 4 | Add 0.3 × 10E+06 cells/75 cm2 flask |
| For Day 5 | Add 0.25 × 1E+06 cells/75 cm2 flask |

4.12. When the cells in the 75 cm² are ready to seed into 96 well assay plates (approximately 80% confluent), remove the media from the flask.
    4.13. Add 5 mLs DPBS to the flask, swirl to rinse all cells and then remove and discard the DPBS.
    4.14. Add 2 mLs 0.25% Trypsin-EDTA to the flask, tip to coat all cells and then remove and discard the trypsin.
    4.15. Add another 2 mLs 0.25% Trypsin-EDTA and again, tip to coat all cells and then place the flask into the 37° C. incubator for 6 minutes or until cells detach.
    4.16. Once the cells are detached, add 8 mLs of complete media, collect the cells and transfer the volume to a 50 mL conical tube.
    4.17. Proceed to "Method for Seeding A549 Cells into 96 Well Assay Plates."

Method for Passaging A549 Cells
1. Materials and Reagents
    1.1. 1549 Human Lung Carcinoma (ATCC—Cat. No.: CCL—185)
    1.2. 25 cm² Flasks (Corning—Cat. No. 431463, or equivalent)
    1.3. 75 cm² Flasks (Corning—Cat. No. 431464, or equivalent)
    1.4. 50 mL tubes (Fisher Scientific—Cat. No.: 14-432-22, or equivalent)
    1.5. DPBS (Lonza—Cat. No.: 17-512F, or equivalent)
    1.6. Hemacytometer
    1.7. RPMI-1640 (+) phenol red (Lonza—Cat. No.: 12-167F, or equivalent)
    1.8. HI-FBS (Gibco—Life Technologies—Cat. No.: 10082-147, or equivalent)
    1.9. 200 mM L-Glutamine (Lonza—Cat. No.: 17-605E, or equivalent)
    1.10. 0.25% Trypsin-EDTA (Gibco—Cat. No.: 25200-056, or equivalent)
2. Instruments
    2.1. Forma Scientific centrifuge with winging bucket rotor (Model 5682, or equivalent)
    2.2. Water bath set at 37° C.
    2.3. Humidified incubator set at 37° C. with 5% Co2
3. Prepared Reagents
    3.1. RPMI-1640 Complete Media
    3.2. 500 mL bottle of RPMI-1640 basal media containing phenol red
    3.3. Add 50 mL HI-FBS
    3.4. Add 5.5 mL of 200 mM L-Glutamine
4. Procedure
    4.1. Monitor the flask daily and when the cells reach approximately 80% confluence, remove the media and wash the cells by adding 2 mL DPBS to the flask. Ensure that all cells are rinsed and discard the DPBS.
    4.2. Add 1 mL 0.25% trypsin-EDTA to prewash the cells, tip flask to coat all cells and discard the trypsin.
    4.3. Add another 1 mL trypsin, tip to coat all cells and then place into a 37° C. incubator for 4 minutes or until cells detach.
    4.4. Stop the trypsin reaction by adding 4 mL complete media to the flask and then collect all cells and transfer to a 50 mL conical tube.

4.5. Count the cell solution using a heacytometer and seed the cells into the appropriate number of 75 cm² flasks as needed using the following seeding densities:

| Day Cell Needed | Seeding Density |
|---|---|
| For Day 3 | Add 0.4 × 10E+06 cells/75 cm2 flask |
| For Day 4 | Add 0.3 × 10E+06 cells/75 cm2 flask |
| For Day 5 | Add 0.25 × 1E+06 cells/75 cm2 flask |

4.6. When the cells in the 75 cm² are ready to seed into 96 well assay plates (approximately 80% confluent), remove the media from the flask.
4.7. Add 5 mLs DPBS to the flask, swirl to risen all cells and then remove and discard the DPBS.
4.8. Add 2 mLs 0.25% Trypsin-EDTA to the flask, tip to coat all cells and then remove and discard the trypsin.
4.9. Add another 2 mLs 0.25% Trypsin-EDTA and again, tip to coat all cells and then place the flask into the 37° C. incubator for 6 minutes or until cells detach.
4.10. Once the cells are detached, add 8 mLs of complete media, collect the cells and transfer the volume to a 50 mL conical tube.
4.11. Proceed to "Method for Seeding A549 Cells Into 96 Well Assay Plates."

Method for Seeding A549 Cells into 96 Well Assay Plates
1. Materials and Reagents
   1.1. 75 cm² Flasks (Corning—Cat. No.: 431464, or equivalent)
   1.2. 50 mL tubes (Fisher Scientific—Cat. No.: 14-432-22, or equivalent)
   1.3. DPBS (Lonza—Cat. No.: 17-512F, or equivalent)
   1.4. Hemacytometer (Fisher Scientific—Cat. No.: S17040, or equivalent)
   1.5. RPMI-1640 (+) phenol red (Lonza—Cat. No.: 12-167F, or equivalent)
   1.6. RPMI-1640 (−) phenol red (Lonza—Cat. No.: 12-918F, or equivalent)
   1.7. Heat-Inactivated FBS (Gibco—Life Technologies—Cat. No.: 10082-147, or equivalent)
   1.8. 200 mM L-Glutamine (Lonza—Cat. No.: 17-605E, or equivalent)
   1.9. 0.25% Trypsin-EDTA (Gibco—Cat. No.: 25200-056, or equivalent)
   1.10. Black 96 well tissue culture-treated assay plates with universal black lids (Costar 3916 and Corning 3935 respectively)*
   1.11. 50 mL reagent reservoir (Fisher Scientific—Cat. No.: 07-200-127, or equivalent)
2. Instruments
   2.1. Forma Scientific centrifuge with swinging bucket rotor (Model: 5682, or equivalent)
   2.2. Water bath set at 37° C. with 5% CO2
   2.3. Finnpipette 12 channel digital pipettor (Fisher Scientific—Cat. No.: 21-377-830, or equivalent)
3. Prepared Reagents
   3.1. RPMI-1640 Complete Media with or without phenol red
      3.1.1. 500 mL bottle of RPMI-1640 basal media
      3.1.2. Add 50 mL heat-inactivated fetal bovine serum
      3.1.3. Add 5.5 mL of 200 mM L-Glutamine
4. Procedure
   4.1. Cells should be approximately 80% confluent in a 75 cm² flask.
   4.2. Remove the medium and wash the cells by adding 5 mL DPBS to the flask. Ensure that all cells are rinsed and then remove and discard the DPBS.
   4.3. Add 2 mL 0.25% trypsin-EDTA to prewash the cells, tip flask to coat all cells and then remove and discard the trypsin.
   4.4. Add another 2 mL trypsin, tip to coat all cells and then place into a 37° C. incubator for 6 minutes or until cells detach.
   4.5. Stop the trypsin reaction by adding 8 mL complete medium to the flask and then collect all cells and transfer to a 50 mL conical tube.
   4.6. Count the cell solution using a hemacytometer and record the cell density.
      4.6.1. Cell density=_____ cells/mL
   4.7. Calculate the number of cells needed for the assay based on the number of plates.
      4.7.1. _____ plates×1E+06 cells/plate=_____ cells needed
   4.8. Calculate the volume of cell suspension required and transfer to 50 mL conical tube.
      4.8.1. Cells needed (Step 4.7)/_____ cell density (Step 4.6)=_____ mL of cell suspension to transfer
   4.9. Add 10-20 mL of complete medium and centrifuge the tubes at 220×g for 5 minutes.
   4.10. Discard the supernatant and then sharply flick the pellet to resuspend the cells in the residual volume left in the tube.
   4.11. Resuspend the cells in the appropriate volume of complete media based on the number of assay plates:
      4.11.1. _____ plates×10 mL/plate=_____ mL complete medium
   4.12. Transfer the suspended cell volume to a 50 mL reservoir and use a multi-channel pipettor to add 100 µL of the cell suspension to the appropriate wells in the 96 well plates according to the following template.

NOTE: Ensure cells are evenly dispersed during this step, resuspending as necessary with pipettor.

| 1 | 2 | 3 | 4 | 5 | 6 | 7 | 8 | 9 | 10 | 11 | 12 |
|---|---|---|---|---|---|---|---|---|---|---|---|
| DPBS | DPBS | DPBS | DPBS | DPBS | DPBS | DPBS | DPBS | DPBS | DPBS | DPBS | DPBS |
| DC | Cells | Cells | Cells | Cells | Cells | Cells | Cells | Cells | Cells | Cells | MC |
| DC | Cells | Cells | Cells | Cells | Cells | Cells | Cells | Cells | Cells | Cells | MC |
| DC | Cells | Cells | Cells | Cells | Cells | Cells | Cells | Cells | Cells | Cells | MC |
| DC | Cells | Cells | Cells | Cells | Cells | Cells | Cells | Cells | Cells | Cells | MC |
| DC | Cells | Cells | Cells | Cells | Cells | Cells | Cells | Cells | Cells | Cells | MC |
| DC | Cells | Cells | Cells | Cells | Cells | Cells | Cells | Cells | Cells | Cells | MC |
| DPBS | DPBS | DPBS | DPBS | DPBS | DPBS | DPBS | DPBS | DPBS | DPBS | DPBS | DPBS |

4.13. Add 200 μL of DPBS to all wells of the top and bottom rows (rows A and H in the plates).
4.14. Add 200 μL of complete media without phenol red to the media control wells (MC).
4.15. Add 100 μL of complete media without phenol red to the drug control wells (DC).
4.16. Switch the clear covers that came with the black plates for black covers and place plates into a humidified incubator set at 37° C. with 5% CO for 24 hours.
NOTE: Retain the clear cover in a sterile environment for the irradiation step in "Method for Irradiating A549 Cells in 96 Well Assay Plates."

Method for Treating A549 Cells with Photofrin®
1. Materials and Reagents
    1.1. 15 mL tubes (Fisher Scientific—Cat. No.: 14-959-49B, or equivalent)
    1.2. RPMI-1640 basal media without phenol red (Lonza—Cat. No.: 12-918F, or equivalent)
    1.3. 50 mL reagent reservoir (Fisher Scientific—Cat. No.: 07-200-127, or equivalent)
    1.4. 0.9% Sterile saline solution (Teknova—S5819, or equivalent)
    1.5. 96 well polypropylene dilution plates (Fischer Scientific—Cat. No.: 07-200-745)
    1.6. Photofrin® vials
2. Instruments
    2.1. Water bath set at 37° C.
    2.2. Humidified incubator set at 37° C. with 5% CO2
    2.3. Finnpipette 12 channel digital pipettor (Fischer Scientific—Cat. No.: 21-377-830, or equivalent)
    2.4. Benchtop rotating shaker (Hoefer Red Rotor, or equivalent)
3. Prepared Reagents
    3.1. RPMI-1640 Complete Medium without phenol red (Complete Medium)
        3.1.1. 500 mL bottle of RPMI-1640 basal medium
        3.1.2. Add 50 mL Heat-Inactivated FBS
        3.1.3. Add 5.5 mL of 200 mM L-Glutamine
4. Procedure
    4.1. Place RPMI-1640 complete media without phenol red (complete medium) into a water bath set at 37° C. for 1 hour prior to beginning treatment.
    4.2. All steps are performed aseptically in a biosafety cabinet.
    4.3. Label four 50 mL conical tubes as follows: Working Reference, Working Test and Cell Control, and Test Concentrate.
    4.4. Aliquot 31.8 mL sterile saline for injection into the Photofrin® tube and set aside.
    4.5. Calculate the volume of complete medium needed based on the number of assay plates and add the calculated volume to each of the labeled 50 mL conical tubes.
        4.5.1. _____ plates×4.72 mL=_____ mL per tube
    4.6. Calculate the volume of saline for injection or Photofrin® solution to be diluted based on the number of assay plates and add the calculated volume to tube labeled Cell Control and mix well.
        4.6.1. _____ plates×280 μL=_____ μL
    4.7. Use the following template to set-up the assay dilution plate.
    4.8. Using a multichannel pipettor, dispense 125 μL of complete media to wells B3-G8 of a dilution plate. Use a separate dilution plate for each assay plate.
    4.9. Dispose of the remaining medium in the reservoir and transfer the volume from the Cell Control tube to the reservoir and then add 125 μL to wells B9-G10 of the dilution plate.
    4.10. Darken the working environment using window coverings as necessary to achieve ambient light less than 0.3 mW/cm$^2$ to ensure that the Photofrin® is not unintentionally activated.
    4.11. Remove sufficient aliquots of the Reference Standard from the freezer and thaw in a 37° C. water bath, disinfect with 70% isopropanol and place in the biosafety cabinet.
    4.12. Remove a vial of Photofrin® form the box, remove the metal seal from the top of the vial, tap the vial on the hood surface to clear powder from the rubber cap and then carefully remove the rubber cap and place inverted on the surface of the hood.
    4.13. Using a 10 mL pipet, transfer the contents of the conical tube labeled T directly to the Photofrin® vial, replace the rubber cap and while holding the vial at the top and bottom, invert multiple times to mix well.
    4.14. Pour the volume back into the 50 mL tube labeled Test Concentrate.
    4.15. Add the appropriate volume calculated in Step 4.6 from the tube labeled T to the tube labeled Working Test and mix well.
    4.16. Mix the contents well and add the appropriate volume calculated in Step 4.6 from the aliquot of Reference Standard to the tube labeled Working Reference and mix well.
    4.17. Prepare a 50 mL reservoir and then transfer the contents from the Working Reference tube to the reservoir.
    4.18. Using a multi-channel pipettor, dispense 125 μL to wells B1-D2 of the dilution plate.
    4.19. Add an additional 125 μL to wells B2-D2 such that the total volume added for those wells is 250 μL.
    4.20. Add 125 μL to wells B11-D11 in the dilution plate.
    4.21. Repeat for each of the assay plates and then discard the remaining volume and reservoir.
    4.22. Prepare another 50 mL reservoir and then transfer the contents from the Working Test tube to the reservoir.
    4.23. Using a multi-channel pipettor, dispense 125 μL to wells E1-G2 of the dilution plate.
    4.24. Add an additional 125 μL to wells E2-G2 such that the total volume added for those wells is 250 μL.
    4.25. Repeat for each of the assay plates and then discard the remaining volume and reservoir.
    4.26. Using a multi-channel pipettor with 6 channels/tips, mix the well volumes in wells B2-G2 of the dilution plate three times and then transfer 125 μL of this volume to wells B3-G3 to create the first dilution.
    4.27. Repeat this dilution scheme with wells B8-G8. After transferring and mixing the volume in wells B8-G8, discard 125 μL instead of transferring to B9-G9.
    4.28. Take the plate with the seeded A549 cells from the incubator and place into biosafety cabinet. Ensure that the cell plate and dilution plates are correctly aligned and then use the multi-channel pipettor fitted with 11 tips to transfer 100 μL from wells A1-D11 of the dilution plate to the corresponding row of the cell plate. Before pulling the volume up, mix each row gently 3 times in the dilution plate and then transfer the volume to the cell plate.
    4.29. Use the multi-channel pipettor fitted with 11 tips to transfer 100 μL from wells E1-H11 of the dilution plate to the corresponding row of the cell plate. Before pulling the volume up, mix each row gently 3 times in the dilution plate and then transfer the volume to the cell plate.

4.30. Replace black cover on the cell plates and place onto a bench-top rotary shaker with the rotation set on low and start the shaker for a total of 20 rotations to mix the well volumes.

4.31. Return the plates to the incubator for 4 hours and then proceed with "Method for Irradiating Photofrin®-treated A549 Cells in 96 Well Plates."

Method for Irradiation Photofrin®-Treated A549 Cells in 96 Well Plates

1. Materials and Reagents
   1.1. DPBS (Lonza—catalog #: 17-512F, or equivalent)
   1.2. RPMI-1640 (−) phenol red (Lonza—catalog #: 12-918F, or equivalent)
   1.3. Retained clear lids from black 96 well tissue culture-treated assay plates (Costar 3916)
   1.4. 50 mL reagent reservoir (Fisher Scientific—catalog #: 07-200-127, or equivalent)
   1.5. Laser safety goggles
   1.6. Foil adhesive plate seals cut into ¾ inch strips (Thermo-Fisher—catalog #: AB-0626)
   1.7. Ice bucket with half water and half ice
   1.8. Waste container for discarded well volumes
2. Instruments
   2.1. Water bath set at 37° C.
   2.2. Humidified incubator set at 37° C. with 5% CO2
   2.3. Finnpipette 12 channel digital pipettor (Fisher Scientific—catalog #: 21-377-830, or equivalent)
   2.4. 1000 Watt Arc Lamp Power Supply (Oriel Model 68820)
   2.5. 1000 Watt Xenon ozone-free arc lamp in a lamp housing with 2 inch condenser (Newport 6271 and Oriel 66921 respectively)
   2.6. Newport 2 inch aluminum liquid filter (Newport 6123)
   2.7. Mirror holder, beam turning assembly—2 inch series (Newport 66246) with 400-630 nm dichroic mirror (Newport 66229)
   2.8. Lenses (Newport KPX229 76.2 diameter×200 mm focal length)
   2.9. Multiple filter holder, 2 In Series, 2×0.75 in Max Thick, 1.8 in Clear Aperture (Newport 6215) fitted with 50% infrared blocking filter (Newport 59042) and 650 nm cut-off filter (Andover Corporation Part No. 650-FL07-50)
   2.10. Multiple Filter Holder, 3 In Series, 3×0.75 in Max Thick, 2.8 in Clear Aperture (Newport 6216)
   2.11. Plastic washer spacers (Newport 6215-503)
   2.12. Peristaltic pump fitted with ⅛" i.d. Tygon tubing for cooling aluminum liquid filter
   2.13. Timer
3. Prepared Reagents
   3.1. RPMI-1640 Complete Media without phenol red
       3.1.1. 500 mL bottle of RPMI-1640 basal medium
       3.1.2. Add 50 mL HI-FBS
       3.1.3. Add 5.5 mL of 200 mM L-Glutamine
4. Procedure
   4.1. Place RPMI-1640 complete medium without phenol red (hereafter referred to as complete medium in this method) and DPBS into a water bath set at 37° C. for 1 hour prior to beginning irradiation procedures.
   4.2. At least 45 minutes prior to irradiation, perform the following steps:
       4.2.1. Dispense about ⅓ volume water into an ice bucket and then add a half volume of ice.
       4.2.2. Place the flow tubing into the ice bucket and submerge the tubing and then fill the ice bucket to the top with ice.
       4.2.3. Turn on the circulator and start the circulating water to at least a 6 mL/minute flow rate.
   4.3. 15 minutes prior to irradiation, perform the following steps:
       4.3.1. Turn on the Xenon lamp power supply and press the "Output Pre-Adjust" button and ensure that the needle moves to 1000 Watts.
       4.3.2. Put on eye protection and then press the "Lamp Start" button on the power supply to ignite the lamp.
       4.3.3. Prepare adhesive foil strips for covering the control wells.
   4.4. After the cells have been incubated with Photofrin® for 4 hours, darken the room and then take the cell plates from the incubator and place into a biosafety cabinet.
   4.5. Using the pre-warmed solutions, fill one reservoir with the DPBS and one with the complete medium.
   4.6. Using a multi-channel pipettor fitted with 12 tips, remove and discard the contents of wells A1-D12, taking care to keep the tips at the edge of the well to minimize monolayer disruption. Discard the tips.
   4.7. Using a multi-channel pipettor fitted with 12 tips, remove and discard the contents of wells E1-H12, taking care to keep the tips at the edge of the well to minimize monolayer disruption. Discard the tips.
   4.8. Carefully add back 200 µL of the pre-warded DPBS to the wells to wash out the drug and then remove and discard this volume.
   4.9. Slowly add back 200 µL of the pre-warmed complete medium to all of the wells.
   4.10. Cover the wells A10-H11 using the adhesive foil strips, taking care that the entire column is blocked and that adjacent non-control columns are not.
   4.11. Replace the black plate cover with a clear one and move the plate to the template stage under the lamp and start irradiation for 10 minutes.
   4.12. After 10 minutes, return the plate to the hood, remove the foil adhesive and replace the black lid.
   4.13. Return the plates to the incubator for 24 hours and then proceed with "Method for XTT staining of Photofrin®-treated A549 cells."

Method for XTT staining of Photofrin®-Treated A549 Cells in 96 Well Assay Plates 1. Materials and Reagents
   1.1. 50 mL tubes (Fisher Scientific—Cat. No. 14-432-22, or equivalent)
   1.2. DPBS (Lonza—Cat. No.: 17-512F, or equivalent)
   1.3. 50 mL reagent reservoir (Fisher Scientific—Cat. No.: 07-200-127, or equivalent)
   1.4. XTT sodium salt (Sigma—Cat No.: X4626, or equivalent)
   1.5. Phenazine methosulfate (Sigma—Cat. No.: P9625)
2. Instruments
   2.1. Water bath set at 37° C.
   2.2. Humidified incubator set at 37° C. with 5% CO2
   2.3. Finnpipette 12 channel digital pipettor (Fisher Scientific—Cat. No.: 21-377-830, or equivalent)
   2.4. Spectramax 340PC plate reader
3. Prepared Reagents
   3.1. XTT staining solution
       3.1.1. Calculate the appropriate amount of XTT powder needed.

3.1.1.1. _____ plates×5 mg/plate=_____ total mg XTT needed
3.1.1.2. Total volume of DPBS needed=mg XTT=_____ mL
3.1.2. Dissolve the XTT powder in the required volume of pre-warmed DPBS.
3.1.3. Add 40 µL of stock PMS to each mL of dissolved XTT powder.
3.1.3.1. _____ mL XTT solution×40 µL of stock PMS=_____ µL of stock PMS 4. Procedure
   4.1. Remove the 96 well treated plates from the incubator and place into the hood.
   4.2. Dispense the XTT staining solution into a 50 mL reservoir.
   4.3. Add 50 µL of the XTT staining solution directly to the wells of the plate and then place the plate into the incubator for 4 or more hours until color change has developed fully.
   4.4. After color development, check the wells for bubbles and remove these using a flamer or other method.
   4.5. Read the plates on a Spectramax plate reader and record the OD values using a 430 nm wavelength.

3. Results of Studies Conducted to Determine the Feasibility of an In Vitro Potency Assay An optical train is constructed allowing the even illumination of a 96-well tissue culture plate. Treatment of cells with Photofrin® followed by irradiation at 400-650 nm results in Photofrin® dose-dependent killing of the cells. An assay system for determining the potency of a test lot of Photofrin® relative to a Reference Standard is established and evaluated for linearity, specificity, and robustness.

Materials and Methods

Cells and Media

A549 human lung carcinoma cells are obtained from ATCC and grown in RPMI medium with 10% heat-inactivated fetal bovine serum and 2% L-glutamine.

Reagents and Materials

Photofrin® (Lot No.: OG067, expiration date Oct. 31, 2012) is obtained from Pinnacle Biologics, Inc. SN-38 is from LKT Labs (Cat. No. CO154; St. Paul, Minn.). Carboplatin is from Sigma (Cat. No. C2538), and Paclitaxel is from Sigma (Cat. No. T1912).

Summary of Procedure

The irradiation apparatus used is shown in FIGS. 1-9 and described above. An overview of the test method is provided in Example 2. A detailed description of the test method is provided in Example 3.

Results

Irradiation Apparatus

The Xenon arc lamp produces a bright, broad wavelength irradiance beam that when collimated still retains a bright center. This lack of homogeneity in the intensity of the light beam has to be minimized in order to achieve even irradiation over the area of the 96-well plate. For this purpose, two plano-convex lenses are introduced into the light path to approximate a Kohler illumination (FIG. 1). After an initial dosing ranging study of Photofrin® (data not shown), each well of an assay plate containing A549 cells is treated equally with Photofrin® at 1.5 µg/mL to assess homogeneity of the irradiation. For this experiment, the percent viability is calculated relative to a second plate of cells without drug. The degree of cell killing is observed to vary significantly with position on the plate, with wells in the middle of the plate showing no killing (103% viability). To address the inhomogeneity in irradiance, the distance from the final bandpass filter to the sample is raised approximately 2-fold from 54 cm to 95.5 cm while the first surface of the plano-convex lenses is maintained at 13.6 cm from the 650 nm cut-off filter. By increasing the length of the light path, the center zone of irradiance is broadened to cover the area of the entire plate (FIG. 13). As the light path is lengthened, the overall irradiance is decreased, necessitating the use of a higher Photofrin® concentration.

Effect of Plate Type

Initial experiments are performed using standard clear 96-well plates. When black plates with black lids are used to perform the assay, a higher $EC_{50}$ is obtained, indicating that extraneous light is reaching the cells in the clear plates and causing additional cell killing (see FIG. 14A and FIG. 14B, Table 1). Use of black plates results in a consistent 4-fold increase in the $EC_{50}$ relative to clear plates.

TABLE 1

Effect of plate type on Photofrin® $EC_{50}$

| Experiment | Clear Plate $EC_{50}$ | Black plate $EC_{50}$ |
|---|---|---|
| PIN-004 | 1.87 | 8.08 |
| PIN-008 | 2.49 | 10.1 |
|  | 2.46 | 9.48 |
|  | 2.33 | 9.59 |
| Mean | 2.29 | 9.31 |

Data from two experiments is shown. The dose response curves of Photofrin® were either nine point (250-0.977 µg/m, PIN-004) or six point (30.0-1.09 µg/mL, PIN-008).

Effect of Chemotherapeutic Drugs

The broadly active chemotherapeutics drugs SN-38 (20 µM top dose), the active metabolite of irinotecan, carboplatin (7.5 mM top dose), and paclitaxel (20 µM top dose) are tested to determine if sufficient cell killing can be achieved under the anticipated assay conditions, i.e., 24 hour incubation with XTT endpoint. None of the drugs produce sufficient cell killing under the assay conditions to allow their use a positive or system suitability control (data not shown).

Selection of Assay Endpoint

XTT and MTT are two types of formazan dyes that are used to measure mitochondrial function as a surrogate for cell viability. A Photofrin® dose response curve is performed with either XTT or MTT as the endpoint. The results obtained with these two endpoints differ by approximately 15%, but each produces consistent values (see Table 2, below). As the potency of an unknown will be determined with respect to a Reference Lot, the absolute $EC_{50}$ value is not critical. Given that the use of the MTT dye requires an additional solubilization step, XTT is selected for use in this assay.

TABLE 2

Comparison of XTT and MTT assay endpoints

| Experiment | $EC_{50}$ - XTT | $EC_{50}$ - MTT |
|---|---|---|
| PIN-009 | 9.48 | 8.28 |
|  | 9.42 | 8.11 |
| Mean | 9.45 | 8.20 |

Positional Effects

The effect of sample position within the 96-well is investigated. The experimental design includes a series of plates where the position of two samples and the controls is altered. The two samples represent a "Standard" sample where the high test concentration on the plate is 70 µg/mL, and a sub-potent "Test" sample where the standard is diluted a further two-fold with medium so that the high test concentration is 35 µg/mL. When the regression analysis is performed, both samples are treated as if the high test concentration is 70 µg/mL, thereby making the Test sample appear to have a potency of one-half of the Standard. The sample arrangement for the various plates is described in Table 3 below. The results of the analysis are compiled in Table 4 below.

TABLE 3

Sample arrangement for positional effects

Sample Placement

| | |
|---|---|
| Plates 1, 4 | Standard, 70 µg/mL, columns 2-8, left to right dilution<br>Test, 35 µg/mL, columns 2-8, left to right dilution<br>Controls in columns 9-11 |
| Plate 2 | Test, 35 µg/mL, columns 2-8, left to right dilution<br>Standard, 70 µg/mL, columns 2-8, left to right dilution<br>Controls in columns 9-11 |
| Plate 3 | Standard, 70 µg/mL, columns 2-8, right to left dilution<br>Test, 35 µg/mL, columns 2-8, right to left dilution<br>Controls in columns 9-11 |
| Plate 5 | Standard, 70 µg/mL, left to right dilution<br>Test, 35 µg/mL, left to right dilution<br>Controls in columns 2-4 |

TABLE 4

Results of positional analysis

| | Standard Sample $EC_{50}$ | Test Sample $EC_{50}$ | −D, +L/CC | +D, −L/CC |
|---|---|---|---|---|
| Plate 1 | 11.1 | 21.2 | 1.00 | 0.994 |
| Plate 2 | 10.7 | 22.2 | 0.941 | 0.926 |
| Plate 3 | 11.2 | 21.5 | 0.992 | 0.981 |
| Plate 4 | 11.0 | 21.5 | 0.947 | 0.928 |
| Plate 5 | 10.8 | 20.1 | 0.985 | 1.00 |
| Mean | 11.0 | 21.3 | 0.973 | 0.967 |
| CV | 1.89 | 3.59 | 2.78 | 3.74 |
| Mean Potency | 0.516 | | | |

Each plate was assayed identically after set-up as described in Table 3. The $EC_{50}$ for each of the two samples on each plate was calculated using Prism. The mean $EC_{50}$ and the coefficient of variation (CV) for each sample across all of the plates were calculated. The mean potency was calculated as the ratio of the $EC_{50}$ (standard)/$EC_{50}$ (test). The ratio of the no drug, irradiated (−D, +L) and with 70 µg/mL drug, no irradiation (+D, −L) to the cell control (CC, no drug, no irradiation) were also calculated.

Assay Linearity

Assay linearity is tested by comparing the experimentally derived potencies to the theoretical potencies of a series of super- and sub-potent test samples. To best mimic test samples of varying potencies, Photofrin® is dissolved in one-fourth the nominal dissolution volume to create a sample with a theoretical potency of 4. Further dilution of this sample in saline is performed to create samples with nominal potencies of 2, 1, 0.5, and 0.25. Each of the five samples is then handled identically as they are diluted with medium prior to addition to the assay plates for potency determination relative to a nominally prepared sample representing a reference lot. The result of these analyses is shown in Table 5, below. At the extreme of the potencies tested, 4 and 0.25, excessive or insufficient cell killing occurs and the $EC_{50}$ can either not be determine or is determined with a wide confidence interval.

These results indicate that lots of test sample with apparent potencies of greater than two or less than 0.5 should be reviewed carefully, and adjustments in the preparation of the test sample should be considered to obtain an appropriate amount of cell killing under the assay conditions.

TABLE 5

Assay linearity

| Theoretical Potency | $EC_{50}$ STD | $EC_{50}$ Test | Experimental Potency | Ratio of Theoretical/Experimental Potency |
|---|---|---|---|---|
| 4 | 10.3 | 2.36* | 4.36* | 0.917* |
| 2 | 10.6 | 5.16 | 2.05 | 0.976 |
| 0.5 | 11.2, 11.2 | 21.3, 21.7 | 0.526, 0.516 | 0.951, 0.969 |
| 0.25 | 11.6 | NC* | NC | NC |

Theoretical and experimental potencies for Photofrin®. Theoretical potency reflects the predicted potency based on the sample preparation. $EC_{50}$ values for the standard sample (70 µg/mL high test drug concentration) and Test (variable high test drug concentration) are shown with the experimentally derived potency obtained as the ratio of the $EC_{50}$(standard)/$EC_{50}$(test).
*The confidence interval on the $EC_{50}$ is wide due to poor curve fitting.
**Not calculable due to poor curve fitting.

Robustness Testing

In the following series of experiments, key assay parameters are deliberately varied to determine the effect of small variations on assay performance. The variations are designed to encompass the normal variation that could be encountered during the routine performance of the assay.

Cell Seeding Density

The number of cells seeded into each well of the 96-well plate is varied from the nominal value of $1.0 \times 10^4$ cells/well. The densities tested are $0.8 \times 10^4$, $1.0 \times 10^4$, and $1.2 \times 10^4$ cells/well. A Standard sample (70 µg/mL high test concentration) and a Test sample (35 µg/mL high test concentration) is assayed on each plate. The expected potency of the Test sample is 0.5. The results of this experiment are shown in Table 6 below. The results indicated that the assay may be sensitive to cell seeding density, and that densities about $1.0 \times 10^4$ may lead to inaccurate potency determination.

TABLE 6

Effect of assay plate seeding density

| Seeding Density | $EC_{50}$ STD | $EC_{50}$ Test | Potency of Test Sample* |
|---|---|---|---|
| $0.8 \times 10^4$ cells/well | 11.0 | 21.1 | 0.521 |
| $1.9 \times 10^4$ cells/well | 11.2 | 21.3 | 0.526 |
| $1.2 \times 10^4$ cells/well | 10.9 | 27.9 | 0.391 |

$EC_{50}$ values for the standard sample (70 µg/mL high test drug concentration) and Test (35 µg/mL high test drug concentration) are shown with the experimentally derived potency obtained as the ratio of the $EC_{50}$(standard)/$EC_{50}$(test).
*The expected potency for each of the conditions was 0.5.

Cell Passage Number

When A549 cells are removed from liquid nitrogen storage, the initial passage number is designated at P1. These cells are continuously passaged during the execution of the experiments described in this report. In preparation for this aspect of robustness testing, a second vial of cells is thawed and cultured. This experiment compares the results obtained with A549 cells at Passage 10 (P10) with those at passage 17 (P17). A Standard sample (70 µg/mL high test concentration) and a Test sample (35 µg/mL high test concentration) is assayed on each plate. The expected potency of the Test sample is 0.5. The results of this experiment are shown in Table 7 below. The P10 data for the Test sample fails to result in a well-fit regression resulting in a wide confidence interval for the $EC_{50}$ value, nevertheless, the calculated potency value is close to the expected value of 0.5. Importantly, the $EC_{50}$ values and the calculated potency of the assay performed with the P17 cells is consistent with P10 data in the assay, and the overall performance of the assay, demonstrating the suitability of the P17 cells.

TABLE 7

Effect of A549 cell passage number

| Seeding Passage | $EC_{50}$ STD | $EC_{50}$ Test | Potency of Test Sample* |
|---|---|---|---|
| P10 | 10.5 | 18.9** | 0.556 |
| P17 | 10.1 | 19.2 | 0.526 |

$EC_{50}$ values for the Standard sample (70 µg/mL high test drug concentration) and Test (35 µg/mL high test drug concentration) are shown with the experimentally derived potency calculated as the ratio of the $EC_{50}$(standard)/$EC_{50}$(test).
*The expected potency for each of the conditions was 0.5.
**Wide confidence interval due to poor curve fitting.

Time of Irradiation

The time of irradiation is varied from the nominal value of 10 minutes to include assays performed at 8, 9, 10, 11, and 12 minutes of light irradiation. A Standard sample (70 µg/mL high test concentration) and a Test sample (35 µg/mL high test concentration) is assayed on each plate. The expected potency of the Test sample is 0.5. The results of this experiment are shown in Table 8 below. The results indicate a trend toward lower $EC_{50}$ values with increasing irradiation time. The effect appears proportional in both samples and potencies within 11% of the expected value of 0.5 is obtained under all of the conditions.

TABLE 8

Effect irradiation time

| Irradiation Time | $EC_{50}$ STD | $EC_{50}$ Test | Potency of Test Sample* |
|---|---|---|---|
| 8 minutes | 12.0 | 24.5 | 0.490 |
| 9 minutes | 12.0 | 25.2 | 0.476 |
| 10 minutes | 11.1 | 22.8 | 0.487 |
| 11 minutes | 11.6 | 20.9 | 0.555 |
| 12 minutes | 10.8 | 21.0 | 0.514 |

$EC_{50}$ values for the Standard sample (70 µg/mL high test drug concentration) and Test (35 µg/mL high test drug concentration) are shown with the experimentally derived potency calculated as the ratio of the $EC_{50}$(standard)/$EC_{50}$(test).
*The expected potency for each of the conditions was 0.5.

Time of Photofrin® Absorption

The amount of time that Photofrin® is allowed to be in contact with the cells is varied from the nominal value of 4 hours to include assays performed at 3.5, 4, and 4.5 hours of Photofrin® absorption. A Standard sample (70 µg/mL high test concentration) and a Test sample (35 µg/mL high test concentration) is assayed on each plate. The expected potency of the Test sample is 0.5. The results of this experiment are shown in Table 9 below. Comparison of the $EC_{50}$ values and the calculated potencies indicate that incubation with Photofrin® for 4.5 hours may affect the absolute value of the $EC_{50}$, but the potency value obtained was within 15% of the expected value of 0.5.

TABLE 9

Effect Photofrin ® absorption time

| Absorption Time | $EC_{50}$ STD | $EC_{50}$ Test | Potency of Test Sample* |
|---|---|---|---|
| 3.5 hours | 10.4 | 19.5 | 0.533 |
| 4.0 hours | 10.2 | 20.1 | 0.507 |
| 4.5 hours | 9.23 | 16.1 | 0.573 |

$EC_{50}$ values for the Standard sample (70 µg/mL high test drug concentration) and Test (35 µg/mL high test drug concentration) are shown with the experimentally derived potency calculated as the ratio of the $EC_{50}$(standard)/$EC_{50}$(test).
*The expected potency for each of the conditions was 0.5.

Post-Irradiation Incubation Time

The amount of time that irradiated plates are incubated before assessment of cell killing is varied from the nominal value of 24 hours to include assays performed with 22, 24, and 26 hours of incubation post-irradiation. A Standard sample (70 µg/mL high test concentration) and a Test sample (35 µg/mL high test concentration) is assayed on each plate. The expected potency of the Test sample is 0.5. The results of this experiment are shown in Table 10 below. Comparison of the $EC_{50}$ values and the calculated potencies indicate that post-irradiation incubation times from 22-26 hours produce potencies within 15% of the expected value.

TABLE 10

Effect post-irradiation incubation time

| Post-irradiation Time | $EC_{50}$ STD | $EC_{50}$ Test | Potency of Test Sample* |
|---|---|---|---|
| 22 hours | 9.16 | 16.7 | 0.549 |
| 24 hours | 10.2 | 18.9 | 0.54 |
| 26 hours | 9.55 | 16.6 | 0.575 |

$EC_{50}$ values for the Standard sample (70 µg/mL high test drug concentration) and Test (35 µg/mL high test drug concentration) are shown with the experimentally derived potency calculated as the ratio of the $EC_{50}$(standard)/$EC_{50}$(test).
*The expected potency for each of the conditions was 0.5.

Post-Irradiation Incubation Temperature

The temperature that irradiated plates are incubated before assessment of cell killing is varied from the nominal value of 37° C. to include assays performed at 35° C., 37° C., and 39° C. A Standard sample (70 µg/mL high test concentration) and a Test sample (35 µg/mL high test concentration) is assayed on each plate. The expected potency of the Test sample is 0.5. The study is conducted in two experiments, each with a nominal temperature assay and one test temperature assay. The results of this experiment are shown in Table 11 below. The results indicate that post-irradiation temperatures between 35° C. and 39° C. have little effect on the $EC_{50}$ or calculated potency of the samples.

TABLE 11

Effect post-irradiation incubation temperature

| Post-irradiation temperature | $EC_{50}$ STD | $EC_{50}$ Test | Potency of Test Sample* |
|---|---|---|---|
| 35° C. | 9.68 | 21.6 | 0.448 |
| 37° C. | 10.8 | 19.9 | 0.543 |
| 37° C. | 9.9 | 20.0 | 0.495 |
| 39° C. | 8.32 | 16.1 | 0.516 |

$EC_{50}$ values for the Standard sample (70 µg/mL high test drug concentration) and Test (35 µg/mL high test drug concentration) are shown with the experimentally derived potency calculated as the ratio of the $EC_{50}$(standard)/$EC_{50}$(test).
*The expected potency for each of the conditions was 0.5.

Different Operators

The assay feasibility is performed primarily by KP, who can be considered an expert in performing the assay. For this study, a second operator, AB, is trained by watching KP perform and assay and then by performing an assay using two assay plates (AB Pilot-1, and -2). AB then performs an assay in parallel with KP to assess inter-operator variability. Each operator assays in parallel two plates containing a Standard sample (70 µg/mL high test concentration) and a Test sample (35 µg/mL high test concentration). The expected potency of the Test sample is 0.5. The results of this experiment are shown in Table 12 below. There are inter-operator differences in the absolute value of the $EC_{50}$ obtained for each sample, with AB consistently obtaining lower values than KP. No clear bias is observed, however, in the calculated potencies for the samples with all of the potency values within 13% of the expected value of 0.5. This suggests that the assay $EC_{50}$ values may be sensitive to inter-operator variability, but that the calculated potency value is robust. As the $EC_{50}$, for a Reference Lot to be included in the system suitability criteria, inter-operator differences in the $EC_{50}$ values should be minimized through a root cause investigation with appropriate corrective action.

TABLE 12

Inter-operator variability

| Operator | $EC_{50}$ STD | $EC_{50}$ Test | Potency of Test Sample* |
|---|---|---|---|
| AB Pilot Assay-1 | 6.62 | 16.1 | 0.411 |
| AB Pilot Assay-2 | 6.76 | 12.6 | 0.537 |
| Inter-operator Assay | | | |
| AB-1 | 6.37 | 13.7 | 0.465 |
| AB-2 | 8.23 | 14.6 | 0.564 |
| Mean | 7.30 | 14.2 | 0.515 |
| KP-1 | 9.45** | 20.1 | 0.470 |
| KP-1 | 9.96 | 19.8 | 0.503 |
| Mean | 0.971 | 20.0 | 04.87 |

$EC_{50}$ values for the Standard sample (70 µg/mL high test drug concentration) and Test (35 µg/mL high test drug concentration) are shown with the experimentally derived potency calculated as the ratio of the $EC_{50}$(standard)/$EC_{50}$(test).
*The expected potency for each of the conditions was 0.5.
**Wide confidence interval due to poor curve fitting.

Summary: Behavior of the Control Samples

Critical aspects of the system suitability will include the acceptable performance of the assay controls. The expectation is that the viability of cells receiving no drug but with light (−D, +L) and cells receiving a high concentration of drug but no light (+D, −L) should approximate the viability of the cell control not receiving drug or light (CC). The results of this analysis for the experiments described in this report, where applicable, are shown in Table 13 below. The percent viability of all samples is based on the CC, which is calculated set at 1.00 and is not included in the Table. The data shows that both of these controls are well-behaved with a mean value equal to the CC, and a coefficient of variation of 6-7%.

TABLE 13

Behavior of controls

| Experiment | −D, +L | +D, −L |
|---|---|---|
| Table 1 | 1.11 | 1.05 |
| | 0.931 | 0.893 |
| | 1.11 | 1.09 |
| | 1.20 | 0.019 |
| | 1.10 | 0.024 |
| | 1.08 | 0.012 |
| Table 2 | 1.11 | 1.06 |
| | 0.994 | 0.947 |
| | 1.06 | 1.06 |
| | 0.997 | 0.986 |
| Table 4 | 1.00 | 0.994 |
| | 0.941 | 0.926 |
| | 0.992 | 0.981 |
| | 0.947 | 0.928 |
| | 0.985 | 1.00 |
| Table 5 | 0.977 | 0.999 |
| | 0.960 | 1.02 |
| | 0.941 | 1.00 |
| | 0.904 | 1.29 |
| | 0.901 | 0.973 |
| Table 6 | 0.993 | 0.990 |
| | 0.994 | 0.981 |
| | 0.993 | 0.977 |

TABLE 13-continued

Behavior of controls

| Experiment | −D, +L | +D, −L |
|---|---|---|
| Table 7 | 0.998 | 0.973 |
| | 0.996 | 1.00 |
| Table 8 | 0.991 | 1.02 |
| | 0.982 | 0.992 |
| | 0.986 | 0.995 |
| | 0.942 | 0.959 |
| | 0.952 | 0.985 |
| Table 9 | 1.02 | 1.01 |
| | 1.03 | 0.898 |
| | 1.06 | 0.959 |
| Table 10 | 1.00 | 1.09 |
| | 1.00 | 1.08 |
| | 0.989 | 0.995 |
| Table 11 | 0.994 | 0.980 |
| | 0.994 | 0.973 |
| | 1.04 | 1.02 |
| | 1.03 | 0.956 |
| Table 12 | 0.906 | 0.990 |
| | 0.937 | 0.906 |
| | 1.00 | 1.03 |
| | 1.08 | 1.02 |
| | 1.02 | 1.00 |
| | 1.01 | 1.02 |
| Mean | 1.00 | 1.00 |
| CV | 0.060 | 0.064 |

Percent viability of the indicated controls is tabulated. The values for +D, −L of 0.019, 0.024, and 0.012 in Table 1 originated from clear plates and showed significant cell killing and were excluded from the analysis. Black plates and lids were used in obtaining all other data in this table.

What is claimed is:

1. A lighting system comprising:
   a lamp housing including a lamp and a light-port, wherein broad spectrum light from the lamp exits the lamp housing through the light-port;
   a first lens to collimate the broad spectrum light that exits the lamp housing through the light-port;
   an infrared absorbing filter to pass a first portion of the collimated broad spectrum light and absorb infrared light of the broad spectrum light that passes through the light-port and that is collimated by the first lens;
   a reflector to reflect the first portion of the collimated broad spectrum light that passes through the infrared absorbing filter;
   a short pass filter to pass a second portion of the collimated broad spectrum light, wherein the second portion of the collimated broad spectrum light comprises a subset of the first portion of the collimated broad spectrum light, and wherein the short pass filter filters out light of the first portion of the collimated broad spectrum light of wavelengths greater than 650 nm and less than 595 nm;
   an infrared blocking filter to pass the second portion of the collimated broad spectrum light after passing through the short pass filter, wherein the infrared blocking filter absorbs residual infrared light of the first portion of the collimated broad spectrum light; and
   a second lens to disperse the second portion of the collimated light that passed through the infrared blocking filter and the short pass filter.

2. A method for studying a photosensitizer, the method comprising:
   adding the photosensitizer to a portion of wells on a cell culture plate to form photosensitizer assay wells, the wells comprising carcinoma cells;
   incubating the photosensitizer assay wells for a first predetermined time period;

optionally washing the photosensitizer assay wells;
irradiating the photosensitizer assay wells with the lighting system of claim 1 at a predetermined wavelength to form irradiated wells, wherein each well is uniformly irradiated;
incubating the irradiated wells for a second predetermined time period; and
determining percent viability of the carcinoma cells contained in the wells.

3. The method according to claim 2, wherein the photosensitizer is a porphyrin-based anti-neoplastic agent.

4. The method according to claim 3, wherein the porphyrin-based anti-neoplastic agent is porfimer sodium.

5. The method according to claim 2, wherein the photosensitizer assay wells are irradiated with light within a range of 400 nm to 650 nm.

6. The method according to claim 2, wherein the carcinoma cells are A549 human lung carcinoma cells.

7. The method according to claim 2, wherein the cell culture plate is an opaque black plate.

8. The lighting system of claim 1, further comprising:
a base positioned on a surface below the second lens;
a ring stand coupled to the base; and
a first support ring removably attached to the ring stand.

9. The lighting system of claim 8,
wherein the second lens comprises a first dispersing lens and a second dispersing lens; and
wherein the first support ring holds the first dispersing lens and the second dispersing lens in place.

10. The lighting system of claim 9,
wherein the first dispersing lens comprises a first plano convex lens;
wherein the second dispersing lens comprises a second plano convex lens;
wherein the first plano convex lens comprises a first plano side and a first convex side;
wherein the second plano convex lens comprises a second plano side and a second convex side; and
wherein the first convex side is adjacent to the second convex side with a gap between the first convex side and the second convex side.

11. The lighting system of claim 1, further comprising:
a wall,
wherein the light-port is located within the wall, and
wherein a position of the second lens is adjustable in at least one of a direction parallel to the wall and a direction perpendicular to the wall.

12. The lighting system of claim 11, further comprising:
a shelf, and
a lens slider including a first hole for passing light;
wherein the shelf comprises a shelf riser parallel to the wall,
wherein the shelf comprises a shelf top perpendicular to the wall,
wherein the shelf top includes a second hole for passing light,
wherein the second lens is removably attached to the lens slider,
wherein the lens slider is removably attached to the shelf top, and
wherein at least a portion of the first hole is above or below at least a portion of the second hole.

13. A method comprising:
using the lighting system of claim 1 to irradiate contents of a cell culture plate.

14. The lighting system of claim 1, wherein the first lens comprises a condenser lens or a Fresnel lens.

15. The lighting system of claim 1, wherein the reflector comprises a dichroic mirror.

16. The lighting system of claim 1, wherein the lamp housing is sealed so that less than 1% of the broad spectrum light from the lamp exits the lamp housing other than through the light-port.

17. The lighting system of claim 1,
wherein the lamp housing comprises a top,
wherein the light-port is within the top,
wherein the first lens is within the light-port, and
wherein the infrared absorbing filter, the infrared blocking filter, the short pass filter, and the second lens are located at positions above the top.

18. The lighting system of claim 1,
wherein the lamp housing comprises a bottom,
wherein the light-port is within the bottom,
wherein the first lens is within the light-port, and
wherein the infrared absorbing filter, the infrared blocking filter, the short pass filter, and the second lens are located at positions below the bottom.

19. The lighting system of claim 1, wherein the collimated broad spectrum light has a spectral range of 400 nm to 700 nm, and wherein the second portion of the collimated broad spectrum light has a spectral range of 595 nm to 645 nm.

* * * * *